United States Patent
Ikeyama et al.

(10) Patent No.: US 11,179,420 B2
(45) Date of Patent: Nov. 23, 2021

(54) METHOD FOR TREATING A DISEASE, COMPRISING ADMINISTERING MESENCHYMAL STEM CELLS OR CULTURE SUPERNATANT THEREOF TO A SUBJECT

(71) Applicant: ROHTO PHARMACEUTICAL CO., LTD., Osaka (JP)

(72) Inventors: Yoshifumi Ikeyama, Osaka (JP); Eiko Uno, Osaka (JP); Masayo Yumoto, Osaka (JP); Mihoko Yoshino, Osaka (JP); Xuan Trung Ngo, Osaka (JP); Hiroyuki Nishida, Osaka (JP); Akiko Uetani, Osaka (JP)

(73) Assignee: ROHTO PHARMACEUTICAL CO., LTD., Osaka (JP)

( * ) Notice: Subject to any disclaimer, the term of this patent is extended or adjusted under 35 U.S.C. 154(b) by 380 days.

(21) Appl. No.: 16/096,973

(22) PCT Filed: Apr. 27, 2017

(86) PCT No.: PCT/JP2017/016836
§ 371 (c)(1),
(2) Date: Oct. 26, 2018

(87) PCT Pub. No.: WO2017/188403
PCT Pub. Date: Nov. 2, 2017

(65) Prior Publication Data
US 2019/0117701 A1    Apr. 25, 2019

Related U.S. Application Data

(60) Provisional application No. 62/343,262, filed on May 31, 2016, provisional application No. 62/328,079, filed on Apr. 27, 2016.

(51) Int. Cl.
*C12N 5/0775* (2010.01)
*A61K 35/28* (2015.01)
*A61P 29/00* (2006.01)

(52) U.S. Cl.
CPC .............. *A61K 35/28* (2013.01); *A61P 29/00* (2018.01); *C12N 5/0663* (2013.01); *C12N 5/0667* (2013.01); *C12N 5/0668* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 2006/0078993 A1 | 4/2006 | Phan et al. | |
| 2006/0233766 A1 | 10/2006 | Messina et al. | |
| 2007/0264269 A1 | 11/2007 | Harmon et al. | |
| 2009/0220464 A1 | 9/2009 | Aggarwal et al. | |
| 2010/0261274 A1 | 10/2010 | Vodyanyk et al. | |
| 2011/0236971 A2 | 9/2011 | Vodyanyk et al. | |
| 2011/0262393 A1 | 10/2011 | Yang et al. | |
| 2012/0251489 A1* | 10/2012 | Herrera Sanchez . | C12N 5/0672 424/85.2 |
| 2013/0190201 A1 | 7/2013 | Dorai et al. | |
| 2013/0195991 A1 | 8/2013 | Ueda et al. | |
| 2013/0337563 A1 | 12/2013 | Phan et al. | |
| 2015/0175971 A1 | 6/2015 | Vodyanyk et al. | |
| 2015/0231180 A1* | 8/2015 | Du ........................ | A61K 35/12 424/93.7 |
| 2015/0307844 A1 | 10/2015 | Sturm | |
| 2016/0024466 A1 | 1/2016 | Phan et al. | |
| 2016/0250257 A1 | 9/2016 | Phan et al. | |
| 2017/0071984 A1 | 3/2017 | Fujimiya et al. | |
| 2017/0198258 A1 | 7/2017 | Jin et al. | |
| 2017/0335409 A1 | 11/2017 | Dorai et al. | |
| 2018/0000866 A1 | 1/2018 | Phan et al. | |
| 2018/0325946 A1 | 11/2018 | Ueda et al. | |
| 2019/0290699 A1 | 9/2019 | Phan et al. | |

FOREIGN PATENT DOCUMENTS

| | | | |
|---|---|---|---|
| CN | 101626772 A | 1/2010 | |
| JP | 2007528705 A | 10/2007 | |
| JP | 2008525489 A | 7/2008 | |
| JP | 2009519978 A | 5/2009 | |
| JP | 2012508733 A | 4/2012 | |
| JP | 5148873 B2 | 2/2013 | |

(Continued)

OTHER PUBLICATIONS

Donnenberg, A. et al. The Cell Surface Proteome of Cultured Adipose Stromal Cells. Cytometry 87A:665-674, 2015. (Year: 2015).*
G. Pachón-Peña et al., "Stromal Stem Cells From Adipose Tissue and Bone Marrow of Age-Matched Female Donors Display Distinct Immunophenotypic Profiles," J. Cell. Physiol., 2011, vol. 226, No. 3, pp. 843-851 (9 pages).
International Search Report issued in International Application No. PCT/JP2017/016836; dated Aug. 1, 2017 (3 pages).
Written Opinion of the International Searching Authority issued in International Application No. PCT/JP2017/016836; dated Aug. 1, 2017 (7 pages).

(Continued)

Primary Examiner — Ralph J Gitomer
(74) Attorney, Agent, or Firm — Osha Bergman Watanabe & Burton LLP

(57) ABSTRACT

An object of the present invention is to provide novel mesenchymal stem cells demonstrating superior therapeutic effects for various diseases, a novel pharmaceutical composition containing the mesenchymal stem cells, and methods for preparing these. The present invention provides mesenchymal stem cells expressing at least one cell surface marker selected from the group consisting of CD201, CD46, CD56, CD147 and CD165. The mesenchymal stem cells expressing such a specific marker are positive for CD29, CD73, CD90, CD105 and CD166, and maintain an undifferentiated state.

6 Claims, 10 Drawing Sheets

(56) References Cited

FOREIGN PATENT DOCUMENTS

| | | |
|---|---|---|
| JP | 2013066473 A | 4/2013 |
| JP | 2013521806 A | 6/2013 |
| JP | 5425399 B2 | 2/2014 |
| JP | 5425400 B2 | 2/2014 |
| JP | 2014240388 A | 12/2014 |
| JP | 2015504662 A | 2/2015 |
| JP | 2015077074 A | 4/2015 |
| WO | 2005001080 A2 | 1/2005 |
| WO | 2005003334 A2 | 1/2005 |
| WO | 2011118795 A1 | 9/2011 |
| WO | 2014128634 A1 | 8/2014 |
| WO | 2015137419 A1 | 9/2015 |
| WO | 2016027850 A1 | 2/2016 |
| WO | 2016043286 A1 | 3/2016 |

OTHER PUBLICATIONS

Elisabetta Mariotti et al., "Comparative Characteristics of Mesenchymal Stem Cells from Human Bone Marrow and Placenta: CD10, CD49d, and CD56 Make a Difference", pp. 1039-1041, No. 6, vol. 17, Stem Cells and Development, Mary Ann Liebert, Inc., New Rochelle, Dec. 8, 2008 (3 pages).

V.L. Battula et al., "Isolation of Functionally Distinct Mesenchymal Stem Cell Subsets using Antibodies against CD56, CD271, and Mesenchymal Stem Cell Antigen-1", pp. 173-184, No. 2, vol. 94, Haematologica, Dec. 9, 2008 (12 pages).

Olga Maslova et al., "Umbilical Cord Tissue-Derived Cells as Therapeutic Agents", pp. 1-10, vol. 2015, Stem Cells International, Jan. 1, 2015 (10 pages).

Zhong-Yang Shen et al., "Bone-marrow mesenchymal stem cells reduce rat intestinal ischemia-reperfushion injury, ZO-1 downregulation and tight junction disruption via a TNF-β-regulated mechanism", pp. 3583-3595, No. 23, vol. 19, World Journal of Gastroenterology, Jan. 1, 2013 (13 pages).

Sa Cai et al., "Transplantation of human bone marrow-derived mesenchymal stem cells transfected with ectodysplasin for regeneration of sweat glands", pp. 2260-2268, Chinese Medical Journal, Jan. 1, 2011 (9 pages).

Siming Yang et al., "Capacity of human umbilical cord-derived mesenchymal stem cells to differentiate into sweat gland-like cells: a preclinical study", pp. 345-353, No. 3, vol. 7, Frontiers of Medicine, Sep. 1, 2013 (9 pages).

Extended European Search Report issued in European Application No. 17789684.2; dated Oct. 22, 2019 (15 pages).

Office Action issued in Chinese Application No. 201780026368.7, dated Apr. 19, 2021 (49 pages).

Office Action issued in Japanese Application No. 2018-514714, dated Apr. 13, 2021 (12 pages).

E. Pierantozzi et al., "Pluripotency regulators in human mesenchymal stem cells: Expression of NANOG but not of OCT-4 and SOX-2", Stem Cells and Development, 2011, vol. 20, No. 5, pp. 915-923 (11 pages).

M. A. Soland et al., "Mesenchymal Stem Cells Engineered to Inhibit Complement-Mediated Damage", PLOS One, Mar. 2013, vol. 8, Issue 3, e60461, pp. 1-8 (9 pages).

* cited by examiner

METHOD FOR TREATING A DISEASE, COMPRISING ADMINISTERING MESENCHYMAL STEM CELLS OR CULTURE SUPERNATANT THEREOF TO A SUBJECT

TECHNICAL FIELD

The present invention relates to mesenchymal stem cells expressing at least one cell surface marker selected from the group consisting of CD201, CD46, CD56, CD147 and CD165, a method for preparing the same, a pharmaceutical composition containing the mesenchymal stem cells and a method for preparing the same.

BACKGROUND ART

In recent years, advances have been made in the development of pharmaceuticals using body cells or tissues and research in regenerative medicine, both of which are attracting considerable attention. In particular, there has been accelerated advancement in the research in ES cells and iPS cells for use in organ regeneration technology and drug development screening. Meanwhile, cell therapy, which uses somatic stem cells (mesenchymal stem cells) isolated from the bone marrow, the adipose tissue or the umbilical cord, is attracting attention as having a higher potential for realization among other forms of regenerative medicine since it uses the inherent functions of somatic stem cells to repair tissue damaged by diseases or other causes, and, for this reason, it is under research. Somatic stem cells (mesenchymal stem cells) are known in general not to be able to differentiate into all organs and tissues, but rather only into specific tissues and organs.

In addition, it is known that somatic stem cells (mesenchymal stem cells) not only have effects on repairing damaged tissues as previously described, but also therapeutic effects on various diseases. For example, somatic stem cells (mesenchymal stem cells) originating in the umbilical cord tissue are known to demonstrate a suppressing effect on reverse immune reactions (graft versus host disease (GVHD)) in transplant recipients having unsuitable histocompatibility with the transplant donor (see Patent Document 1). Furthermore it is also known that mesenchymal stem cells derived from a specific umbilical cord tissue can be used to treat Parkinson's disease (see Patent Document 2) and mesenchymal stem cells derived from another specific umbilical cord tissue demonstrate a therapeutic effect on diseases of the circulatory system (see Patent Document 3). However, the therapeutic effects for various diseases of these mesenchymal stem cells cannot be said to be adequate.

Patent Documents 4 to 6 disclose therapeutic cell compositions containing cells derived from umbilical cord tissues. The cells derived from the umbilical cord tissues contained in each of these therapeutic cell compositions highly express interleukin 8, reticulon 1 and chemokine receptor (C—X—C motif) ligand 3, and further secrete MCP-1, MCP1β, IL-6, GCP-2, HGF, KGF, FGF, HB-EGF, BDNF, TPO, RANTES and TIMP1. It is also disclosed that stem cells isolated from umbilical cord or amnion thereof express genes of various cytokines (Patent Documents 7 and 8). Besides, it is disclosed that a composition containing mesenchymal stem cells derived from umbilical cord blood is used in treatment of nervous diseases, and that a culture broth of these mesenchymal stem cells contains activin A, PF4, decorin, galectin 3, GDF15 and the like (Patent Document 9).

PRIOR ART DOCUMENTS

Patent Documents

Patent Document 1: JP-T 2009-519978
Patent Document 2: JP-T 2008-525489
Patent Document 3: JP-T 2007-528705
Patent Document 4: JP-5425399
Patent Document 5: JP-5425400
Patent Document 6: JP-5148873
Patent Document 7: JP-A 2013-066473
Patent Document 8: JP-A 2015-504662
Patent Document 9: JP-A 2014-240388

DISCLOSURE OF THE INVENTION

Problems to be Solved by the Invention

With the foregoing in view, an object of the present invention is to provide novel mesenchymal stem cells demonstrating superior therapeutic effects against various diseases as well as a method for preparing these mesenchymal stem cells, a novel pharmaceutical composition containing these mesenchymal stem cells, and a method for preparing this pharmaceutical composition.

Means for Solving the Problems

As a result of extensive studies to solve the aforementioned problems, the inventors of the present invention found that a pharmaceutical composition containing certain mesenchymal stem cells demonstrates superior therapeutic effects against various diseases, and the present invention was made. The gist of the present invention is as indicated below.

(1) Mesenchymal stem cells expressing at least one cell surface marker selected from the group consisting of CD201, CD46, CD56, CD147 and CD165.

(2) The mesenchymal stem cells described in (1), which are positive for CD29, CD73, CD90, CD105 and CD166.

(3) The mesenchymal stem cells described in (1) or (2), which secrete Crossveinless-2 and Ectodysplasin A2.

(4) The mesenchymal stem cells described in any one of (1) to (3), which further secrete at least one selected from the group consisting of activin A, Dkk-3, decorin, HGF, Dkk-1, progranulin, GDF-15, angiopoietin-1, CCL28 (VIC), latent TGF-β binding protein 1 (Latent TGF-beta bp1), GDF1, VEGF-C, BTC (betacellulin), Nidogen-1, GLO-1 (glyoxalase-1), sgp130 (soluble gp130), Chordin-Like 2 and EMAP-II.

(5) The mesenchymal stem cells described in any one of (1) to (4), which are derived from umbilical cord, adipose or bone marrow.

(6) A pharmaceutical composition containing the mesenchymal stem cells described in any one of (1) to (5) and/or culture supernatant thereof.

(7) The pharmaceutical composition described in (6), wherein, in the case the pharmaceutical composition contains mesenchymal stem cells, the ratio of mesenchymal stem cells expressing at least one cell surface marker selected from the group consisting of CD201, CD46, CD56, CD147 and CD165 is 70% or more of all mesenchymal stem cells contained in the pharmaceutical composition.

(8) The pharmaceutical composition described in (7), wherein, in the case the pharmaceutical composition contains mesenchymal stem cells, the ratio of mesenchymal stem cells expressing at least one cell surface marker selected from the group consisting of CD201, CD46, CD56, CD147 and CD165 is 90% or more of all mesenchymal stem cells contained in the pharmaceutical composition.

(9) The pharmaceutical composition described in any one of (6) to (8), which is used to prevent or treat a disease selected from the group consisting of cancer, precancerous symptoms, inflammatory diseases, immune diseases, neurodegenerative diseases, metabolic diseases, cardiovascular diseases, heart diseases, bone diseases, gastrointestinal diseases, lung diseases, liver diseases, kidney diseases and oral diseases.

(10) The pharmaceutical composition described in (9), which is used to prevent or treat a disease selected from the group consisting of cancer, precancerous symptoms, inflammatory diseases, cardiovascular diseases, heart diseases, lung diseases, liver diseases and oral diseases.

(11) The pharmaceutical composition described in (10), which is used to prevent or treat a disease selected from the group consisting of lung cancer, myocarditis, cardiac hypertrophy, arteriosclerosis, lung/respiratory inflammation, chronic obstructive pulmonary disease (COPD), hepatitis, liver cirrhosis and periodontal disease.

(12) The pharmaceutical composition described in any one of (6) to (11), which is used to prevent or treat diseases caused by a decrease in the barrier function of the epithelium or endothelium, or diseases in which IL-1 is involved.

(13) The pharmaceutical composition described in (12), wherein the decrease in barrier function is caused by a decrease in the function of tight junctions in the epithelial or endothelial cell layer.

(14) A method for preparing mesenchymal stem cells expressing at least one cell surface marker selected from the group consisting of CD201, CD46, CD56, CD147 and CD165, including a step for inducing, concentrating or isolating and sorting mesenchymal stem cells expressing the marker.

(15) A method for preparing a pharmaceutical composition used to prevent or treat disease, including a step for inducing, concentrating or isolating and sorting mesenchymal stem cells expressing at least one cell surface marker selected from the group consisting of CD201, CD46, CD56, CD147 and CD165.

(16) The method for preparing a pharmaceutical composition described in (15), wherein the disease is selected from the group consisting of cancer, precancerous symptoms, inflammatory diseases, immune diseases, neurodegenerative diseases, metabolic diseases, cardiovascular diseases, heart diseases, bone diseases, gastrointestinal diseases, lung diseases, liver diseases, kidney diseases and oral diseases.

(17) A method for preventing or treating a disease, which uses mesenchymal stem cells expressing at least one cell surface marker selected from the group consisting of CD201, CD46, CD56, CD147 and CD165 and/or a culture supernatant thereof.

(18) The method described in (17), wherein the mesenchymal stem cells are positive for CD29, CD73, CD90, CD105 and CD166.

(19) The method described in (17) or (18), wherein the mesenchymal stem cells secrete Crossveinless-2 and Ectodysplasin-A2.

(20) The method described in (19), wherein the mesenchymal stem cells further secrete at least one selected from the group consisting of activin A, Dkk-3, decorin, HGF, Dkk-1, progranulin, GDF-15, angiopoietin-1, CCL28 (VIC), latent TGF-β binding protein 1 (Latent TGF-beta bp1), GDF1, VEGF-C, BTC (betacellulin), Nidogen-1, GLO-1 (glyoxalase-1), sgp130 (soluble gp130), Chordin-Like 2 and EMAP-II.

(21) The method described in any one of (17) to (20), wherein the mesenchymal stem cells are derived from umbilical cord, adipose or bone marrow.

(22) The method described in any one of (17) to (21), wherein the disease is selected from the group consisting of cancer, precancerous symptoms, inflammatory diseases, immune diseases, neurodegenerative diseases, metabolic diseases, cardiovascular diseases, heart diseases, bone diseases, gastrointestinal diseases, lung diseases, liver diseases, kidney diseases and oral diseases.

(23) The method described in (22), wherein the disease is selected from the group consisting of cancer, precancerous symptoms, inflammatory diseases, cardiovascular diseases, heart diseases, lung diseases, liver diseases and oral diseases.

(24) The method described in (23), wherein the disease is selected from the group consisting of lung cancer, myocarditis, cardiac hypertrophy, arteriosclerosis, lung/respiratory inflammation, chronic obstructive pulmonary disease (COPD), hepatitis, liver cirrhosis and periodontal disease.

(25) The method described in any one of (17) to (24), wherein the disease is a disease caused by a decrease in the barrier function of the epithelium or endothelium, or a disease in which IL-1 is involved.

(26) The method described in (25), wherein the decrease in the barrier function is caused by a decrease in the function of tight junctions in the epithelial or endothelial cell layer.

Effects of the Invention

Mesenchymal stem cells expressing at least one cell surface marker selected from the group consisting of CD201, CD46, CD56, CD147 and CD165 are characterized as cells which, in addition to demonstrating superior action that inhibits the production of inflammatory cytokines from macrophages and other immune cells and action that enhances barrier function, are resistant to oxidative stress and less susceptible to damage. Besides, a culture supernatant of mesenchymal stem cells expressing the aforementioned specific marker demonstrates an effect of appropriately adjusting gene expression relating to inflammation or fibrosis by acting on cardiac myocytes, blood endothelial cells, lung epithelial carcinoma cells, hepatic stellate cells, gingival fibroblasts or the like. Consequently, the pharmaceutical composition of the present invention, which contains these mesenchymal stem cells and/or a culture supernatant thereof, demonstrates superior therapeutic effects against various diseases such as cancer, precancerous symptoms, inflammatory diseases, immune diseases, neurodegenerative diseases, metabolic diseases, cardiovascular diseases, heart diseases, bone diseases, gastrointestinal diseases, lung diseases, liver diseases, kidney diseases or oral diseases.

BEST MODE FOR CARRYING OUT THE INVENTION

Figure 1:
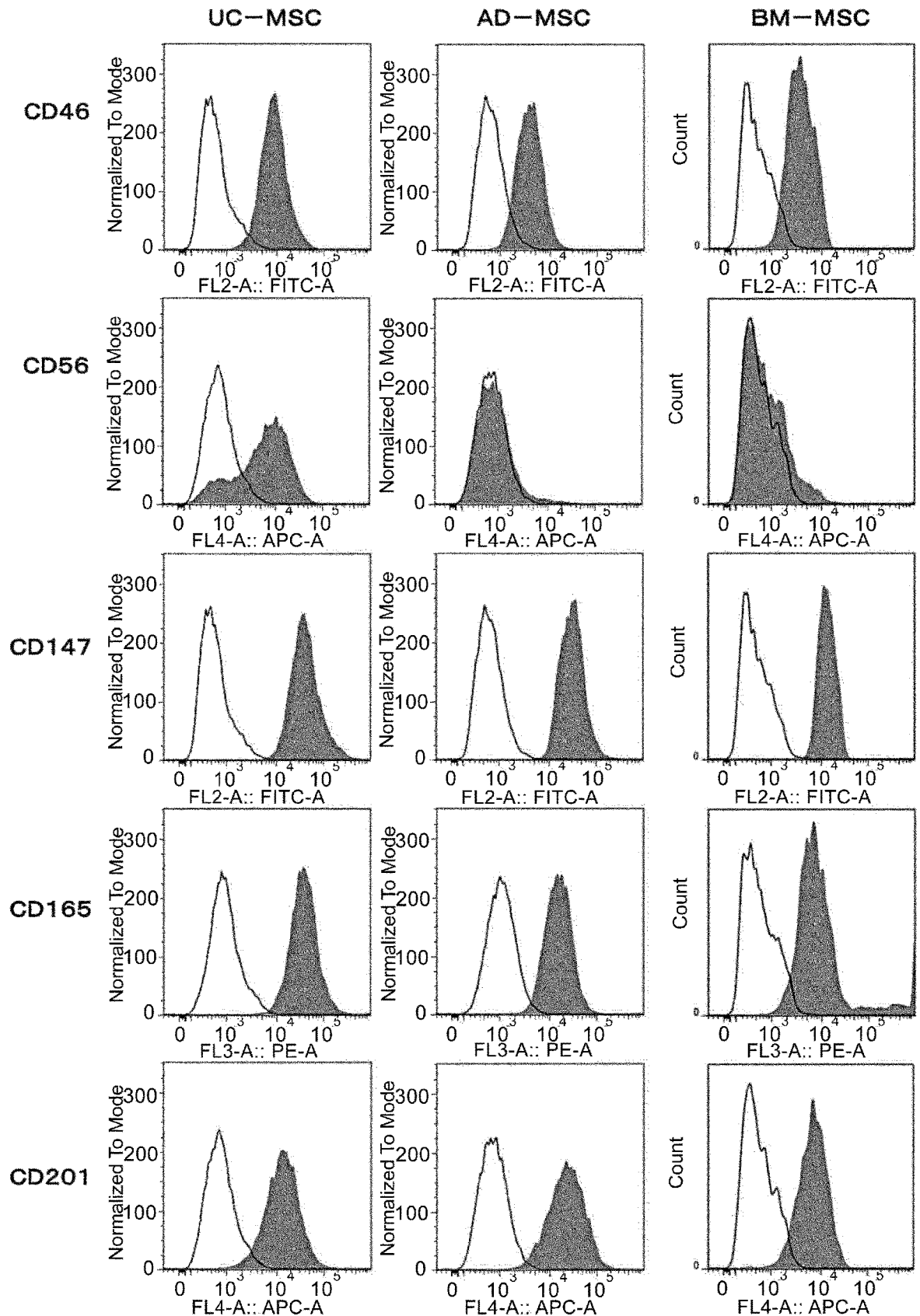
FIG. 1 depicts graphs indicating expression of cell surface markers by mesenchymal stem cells according to the present invention.

Mesenchymal stem cells of the present invention expressing at least one cell surface marker (hereinafter sometimes referred to as the "specific marker") selected from the group consisting of CD201, CD46, CD56, CD147 and CD165 have properties of superior actions to inhibit production of inflammatory cytokines such as IL-6 and to enhance a barrier function. The mesenchymal stem cells also demonstrate an effect of appropriately adjusting gene expression relating to inflammation or fibrosis by acting on cardiac myocytes, vascular endothelial cells, lung epithelial carcinoma cells, hepatic stellate cells, gingival fibroblasts or the like. Besides, the mesenchymal stem cells of the present invention secrete Crossveinless-2 and Ectodysplasin-A2, and also secrete a specific cytokine selected from activin A, Dkk-3, decorin, HGF, Dkk-1, progranulin, GDF-15, angiopoietin-1, CCL28 (VIC), latent TGF-β binding protein 1 (Latent TGF-beta bp1), GDF1, VEGF-C, BTC (betacellulin), Nidogen-1, GLO-1 (glyoxalase-1), sgp130 (soluble gp130), Chordin-Like 2 and EMAP-II, and hence have functions of these cytokines in addition to the aforementioned properties. Besides, the mesenchymal stem cells of the present invention maintain an undifferentiated state while simultaneously efficiently differentiating into cells having a target function under differentiation conditions. Thus, a pharmaceutical composition of the present invention containing the mesenchymal stem cells expressing the specific marker and/or a culture supernatant thereof demonstrates superior therapeutic effects against various diseases. The mesenchymal stem cells expressing the specific marker, the culture supernatant thereof, the pharmaceutical composition containing the same and the like of the present invention will now be described.

[Mesenchymal Stem Cells Expressing Specific Marker]

In the present invention, mesenchymal stem cells refer to cells having the capacity to differentiate into cells belonging to the mesenchyme system such as osteocytes, cardiac myocytes, chondrocytes, tendon cells or adipocytes, and are able to grow while maintaining this capacity to differentiate. Examples of mesenchymal stem cells include mesenchymal stem cells derived from bone marrow, adipose tissue, blood, periosteum, dermis, umbilical cord, placenta, amnion, chorion, deciduous membrane, muscle, endometrium, dermis, dental follicle, periodontal membrane, dental pulp or tooth germ, preferably include mesenchymal stem cells derived from umbilical cord, adipose tissue or bone marrow, more preferably include mesenchymal stem cells derived from umbilical cord. Here, the term "derived" indicates that the aforementioned cells have been acquired, grown or manipulated in vitro from tissue serving as a supply source thereof. Furthermore, the mesenchymal stem cells expressing the specific marker of the present invention are aggregates of the aforementioned mesenchymal stem cells, and may be aggregates containing multiple types of mesenchymal stem cells having mutually different properties, or may be aggregates of substantially homogeneous mesenchymal stem cells.

The mesenchymal stem cells of the present invention may be autologous cells derived from a subject or heterologous cells derived from a different subject of the same species. The mesenchymal stem cells are preferably heterologous cells.

The term "expressing the specific marker" refers to that the mesenchymal stem cells express a specific marker gene, express a specific marker protein, or express both of these. In other words, the term refers to that the mesenchymal stem cells express a gene and/or a protein of at least one cell surface marker selected from the group consisting of CD201, CD46, CD56, CD147 and CD165. Here, determination whether or not the mesenchymal stem cells express each marker can be made, with respect to gene expression, by a conventionally known method using, for example, a gene chip array or a polymerase chain reaction (reverse transcriptase PCR, real-time PCR, or conventional PCR). Besides, with respect to protein expression, the determination can be made by a conventionally known method such as FACS analysis (flow cytometry) using an antibody specifically binding to each marker protein, or enzyme linked immuno sorbent assay (ELISA). In either case, cells not expressing each marker gene or protein are used as a negative control to determine the presence or absence and the level of expression.

The mesenchymal stem cells of the present invention express at least one cell surface marker selected from the group consisting of CD201, CD46, CD56, CD147 and CD165. In other words, the mesenchymal stem cells of the present invention express at least any one of CD201, CD46, CD56, CD147 and CD165, preferably express any two of these, more preferably express any three of these, even more preferably express any four of these, and particularly preferably express all of these. The mesenchymal stem cells expressing the aforementioned specific marker demonstrate superior anti-inflammatory action, anti-fibrotic action, barrier function enhancing action, antioxidant capacity and the like.

CD201 is a molecule also known as an endothelial protein C receptor (EPCR). CD201 is strongly expressed in endothelial cells of arteries and veins of the heart and the lung, and is more weakly expressed in capillaries of the heart and the skin. It is expressed also in dendritic cells, monocytes, leukocytes and some tumor cells. The principal action of CD201 is anticoagulation. CD201 is bonded with protein C with high affinity to increase activation of protein C by a thrombin-thrombomodulin complex. In addition, CD201 plays significant roles in a large number of pathophysiological processes including infection, trauma, blood formation and inflammatory response to autoimmune response.

CD46 is a transmembrane glycoprotein consisting of four isoforms. CD46 is expressed in almost all nucleated cells, functions as a regulator for a complement function through binding with complement components C3b and C4b, and works for host defense against self-complement attack. CD46 is designated as pathogen magnet, and is known to be involved in infection with some pathogens including measles virus, human herpesvirus 6, group A *Streptococcus* and *Neisseria*.

CD56 is an isoform of a neural cell adhesion molecule (N-CAM) having a molecular weight of 140 kDa, and is an antigen useful as a marker for NK cells. CD56 is expressed, with intermediate strength, in subpopulations of large granular lymphocytes (LGL) of peripheral blood and all cells having natural killer activity. Besides, it is expressed in some of subsets of T cells, myeloid cells and myelomas.

CD147 is a type I single-pass transmembrane protein, and is known also as basigin or extracellular matrix metalloproteinase inducer (EMMPRIN). CD147 is expressed in a variety of cells including epithelial cells, endothelial cells, leukocytes and cancer cells. Although it is expressed in vascular epithelium in a non-neoplastic area of the brain and cancer cells, it is not expressed in blood vessels having malignant glioma growth. CD147 is known to have various physiological and pathological activities. In particular, its function as a matrix metalloprotease (MMP) inducer is most well known. In addition, it has been revealed that it is involved in lymphocyte response, expression of a monocarboxylic acid transporter and control of spermatogenesis.

CD165 is a membrane surface glycoprotein of 37 to 47 kDa, and is expressed in most thymocytes, thymic epithelial cells, almost all platelets, fibroblasts, T-cell acute lymphoblastic leukemia (T-ALL) cells, neurons of central nervous tissues, pancreatic islet cells of the pancreas, and Bowman's capsule of the kidney. CD165 is known to be involved in a bond between thymocytes and thymic epithelial cells in the cell differentiation process.

In addition to being characterized by expressing the above-described specific marker, the mesenchymal stem cells of the present invention may also be characterized by their growth characteristics (such as population doubling capacity or doubling time from subculturing to senescence), karyotype analysis (such as having a normal karyotype, maternal lineage or neonatal lineage), surface marker expression except for the above-described surface marker as determined by flow cytometry (for example, FACS analysis), immunohistochemistry and/or immunocytochemistry (such as by epitope detection), gene expression profiling (by, for example, using a gene chip array, reversed transcription PCR, real-time PCR, conventional PCR or other types of polymerase chain reaction), miRNA expression profiling, protein array, cytokine or other protein secretion (using, for example, plasma coagulation analysis, ELISA or cytokine array), metabolites (metabolomic analysis), or other methods known in the art. The mesenchymal stem cells expressing the specific marker of the present invention have, for example, the characteristics indicated below.

(Expression of Surface Marker Except Specific Marker)

The mesenchymal stem cells expressing the specific marker of the present invention express CD29, CD73, CD90, CD105 and CD166 as indicators of undifferentiation.

(Gene Expression Except Specific Marker)

The mesenchymal stem cells expressing the specific marker of the present invention may also be characterized by the presence or absence of the expression of other genes in addition to the specific marker gene. Examples of genes expressed by the mesenchymal stem cells expressing the specific marker of the present invention include MT1X, NID2, CPA4, DKK1, ANKRD1, TIMP3, MMP1, osteoprotegerin (TNFRSF11B), IGFBP5 and SLC14A1. The mesenchymal stem cells expressing the specific marker of the present invention preferably express at least one type of gene selected from the group consisting of MT1X, NID2, CPA4, DKK1, ANKRD1, TIMP3, MMP1, osteoprotegerin (TNFRSF11B), IGFBP5 and SCL14A1. More preferably, the mesenchymal stem cells expressing the specific marker express 2 or more types, 3 or more types, 4 or more types or 5 or more types of the aforementioned genes, and even more preferably, express 6 or more types, 7 or more types, 8 or more types or 9 or more types, and particularly preferably, express all of the aforementioned genes.

Here, the expression of each gene can be measured by methods known among persons with ordinary skill in the art. For example, the expression of each gene can be analyzed by preparing mRNA from the cells in accordance with routine methods and by carrying out RT-PCR on the gene for which the presence or absence and the degree of expression is desired to be ascertained.

MT1X is a cysteine-rich, low molecular weight protein (molecular weight: 500 Da to 14,000 Da) that is localized in the membranes of Golgi bodies. Although details of the function of MT1X are unknown, a possibility has been suggested that it is involved in the defense mechanism against oxidative stress as an anti-oxidative protein. In addition, MT1X is said to be a protein that serves as an indicator for cell undifferentiation. The effect of mesenchymal stem cells expressing the specific marker of the present invention expressing MTX is that the cells are oxidative stress tolerant, which is preferable in that they are more damage-resistant.

NID2 binds to laminin γ1 chain and is a protein involved in the formation and maintenance of the basal membranes by linking laminin to type IV collagen. NID2 is expressed in nearly all the basal membranes in the central nervous system tissue. One possible effect of the mesenchymal stem cells expressing the specific marker of the present invention expressing NID2 is thought to be an improved capacity to differentiate into muscle cells (and particularly, into skeletal muscle and cardiac muscle cells).

CPA4 is one of the proteases that cleave the C-terminal amino acid of proteins. In addition, CPA4 is a protein also known as a prostate cancer marker, and its expression is known to increase in proportion to the malignancy of the cancer. Since the expression of CPA4 tends to increase in actively growing, highly undifferentiated cells, the mesenchymal stem cells expressing the specific marker of the present invention expressing CPA4 may suggest that the mesenchymal stem cells expressing the specific marker demonstrate high levels of undifferentiation and growth.

ANKRD1 is a protein expressed not only by mesenchymal stem cells, but also by cardiac myocytes, smooth muscle cells, fibroblasts and hepatic stellate cells. It is a transcription factor that acts in conjunction with differentiation processes and stress. This gene has also been found to be involved in numerous heart diseases. In addition, it is known that the expression of ANKRD1 increases in fibroblasts during wound healing processes and hepatic stellate cells during liver disorders. The healing of wounds is delayed in ANKRD1-deleted mice (Susan E. Samaras, et al, The American Journal of Pathology, Vol. 185, No. 1, January 2015; and, Inga Mannaerts, et al, Journal of Hepatology 2015). Furthermore, ANKRD1 is also a nuclear factor that controls the expression of MMP10, MMP13 and other extracellular matrix degrading enzymes (Karinna Almodovar-Garcia, et al, MCB 2014). Accordingly, the possible effects of mesenchymal stem cells expressing the specific marker of the present invention expressing ANKRD1 are thought to include an improved capacity to differentiate into cardiac myocytes, enhanced wound healing effects and involvement in remodeling of the extracellular matrix of the fibrotic tissue.

DKK1 is a protein that functions as a Wnt signaling inhibitor and is thought to be involved in the inhibition of canonical pathways. Consequently, it improves bone differentiation capacity by promoting bone differentiation. The expression of DKK1 is known to decrease in osteoporosis. Meanwhile, it is thought to have a beneficial effect on maintaining undifferentiation and growth of cells, and is also known to contribute to fetal development.

TIMP3 (Tissue Inhibitor of Metalloproteinase 3) inhibits activation of MMP1, MMP2, MMP3, MMP9 and MMP13. Moreover, since MMP3 is involved in the activation of numerous other MMPs, TIMP3 functions as a wide-range MMP inhibitory factor. In addition, TIMP3 is also known to inhibit vascularization by inhibiting binding of VEGF to VEGFR2 as well as to function as an apoptosis promoting signal.

MMP1 (matrix metalloproteinase 1) is a protein that degrades type I, type II, type III and type IV collagen. Since it targets major ECMs, it is known to function during cell division and chemotaxis. Expression of MMP1 is also known to increase in response to an inflammatory reaction, and it is involved in tissue destruction and remodeling during inflammation.

Osteoprotegerin (TNFRSF11B) is a decoy receptor of an osteoclast differentiation factor (RANKL) and inhibits activation of NF-κB signaling mediated by RANK. It is produced by osteoblasts, fibroblasts and hepatocytes, and inhibits differentiation of osteoclast progenitor cells into osteoclasts. The local administration of osteoprotegerin has been reported to promote osteogenesis, while conversely to induce osteoporosis as a result of a knockdown.

IGFBP-5 is a protein that binds insulin-like growth factor and nearly all IGFs are present in a form bound to IGFBPs. One function of IGFBP is the enhancement of IGF signaling. In addition, IGFBP-5 is known to inhibit TNFα signaling as a result of promoting the gene expression of TNFR1 while also acting antagonistically on the TNFR1 protein. In addition, IGFBP-5 has been reported to promote cell adhesion and to increase cell viability in breast cancer cells, as well as to inhibit chemotaxis.

SLC14A1 is a urea transporter that is highly expressed in the kidneys and controls intracellular urea concentrations. It has also been shown to be expressed in mesenchymal stem cells and its expression has been reported to decrease during cartilage differentiation in particular.

(MicroRNA Expression)

The mesenchymal stem cells expressing the specific marker of the present invention may also be characterized by the presence or absence of the expression of miRNA. Examples of miRNA expressed by the mesenchymal stem cells of the present invention include hsa-miR-145-5p, hsa-miR-181a-5p, hsa-miR-29b-3p, hsa-miR-34a-5p, hsa-miR-199b-5p, hsa-miR-503-5p, hsa-let-7e-5p, hsa-miR-132-3p, hsa-miR-196a-5p, hsa-miR-324-3p, hsa-miR-328-3p, hsa-miR-382-5p and hsa-let-7d-5p. The mesenchymal stem cells of the present invention preferably express at least one type of microRNA selected from the group consisting of hsa-miR-145-5p, hsa-miR-181a-5p, hsa-miR-29b-3p, hsa-miR-34a-5p, hsa-miR-199b-5p, hsa-miR-503-5p, hsa-let-7e-5p, hsa-miR-132-3p, hsa-miR-196a-5p, hsa-miR-324-3p, hsa-miR-328-3p, hsa-miR-382-5p and hsa-let-7d-5p. The mesenchymal stem cells of the present invention more preferably express 2 or more types, 3 or more types, 4 or more types, 5 or more types or 6 or more types of the aforementioned microRNA, even more preferably express 7 or more types, 8 or more types, 9 or more types, 10 or more types, 11 or more types or 12 or more types, and particularly preferably express all of the aforementioned microRNA.

Furthermore, the expression of microRNA at this point of time can be measured in accordance with methods known among persons with ordinary skill in the art. For example, the expression of microRNA in cells can be analyzed by preparing mRNA from the cells in accordance with routine methods and carrying out qRT-PCR or using a commercially available microRNA array.

(Cytokine Secretion)

The mesenchymal stem cells expressing the specific marker of the present invention may be further characterized by the presence or absence of secretion of the following specific cytokines. The mesenchymal stem cells of the present invention secrete Crossveinless-2 and Ectodysplasin-A2.

The mesenchymal stem cells of the present invention more preferably further secrete at least one selected from the group consisting of activin A, Dkk-3, decorin, HGF, Dkk-1, progranulin, GDF-15, angiopoietin-1, CCL28 (VIC), latent TGF-β binding protein 1 (Latent TGF-beta bp1), GDF1, VEGF-C, BTC, Nidogen-1, GLO-1 (glyoxalase-1), sgp130 (soluble gp130), Chordin-Like 2 and EMAP-II, particularly preferably further secrete at least one selected from the group consisting of activin A, Dkk-3, decorin, HGF, Dkk-1, progranulin, GDF-15, angiopoietin-1, CCL28 (VIC), latent TGF-β binding protein 1 (Latent TGF-beta bp1), GDF1 and VEGF-C, and most preferably further secrete at least one selected from the group consisting of activin A, Dkk-3, decorin, HGF, Dkk-1, progranulin, GDF-15 and angiopoietin-1.

Crossveinless-2 (CV-2) is a bone morphogenetic protein (BMP)-binding protein also known as a BMPER (BMP binding endothelial regulator).

Ectodysplasin-A2 (EDA-A2) is a ligand for the TNF receptor superfamily, and is known to be involved in development of various organs differentiated from the ectoderm, such as hair, tooth and sweat glands.

Angiopoietin-1 is a glycoprotein promoting vasculogenesis or angiogenesis.

Activin A is a homodimer of a protein also known as inhibin beta A (inhibin INHBA). It is known that INHBA is encoded by the INHBA gene in a human.

It has been reported that Dkk-1 binds to LRP-5/-6 as a secretory protein to extracellularly control Wnt signaling to be negative. Dkk-3 performs, through a different mechanism from Dkk-1, cell growth inhibition and apoptosis induction, and is regarded as a molecule for controlling inhibition of canceration/induction of cancer cell death.

Decorin is a proteoglycan having an average molecular weight of about 90 to about 140 kDa. Decorin belongs to the small leucine-rich proteoglycan (SLRP) family, and contains a protein core including leucine repeats having glycosaminoglycan (GAG) consisting of chondroitin sulfate (CS) or dermatan sulfate (DS). Decorin is expressed ubiquitously in the body and is known to be involved in the aggregation of collagen fibers and the proliferation of cells. Examples of the expected effects of increased secretion of decorin in the mesenchymal stem cells expressing the specific marker of the present invention include the effect of repairing tissues at sites of inflammation and tissue damage and the effect of promoting cell growth in tissues.

HGF is a hepatocyte growth factor.

Progranulin (PGN) is a precursor of granulin. Progranulin is a single precursor protein having 7.5 repeats of highly preserved 12-cystein granulin/epithelin motif, and granulin (GRN) belongs to a glycosylated peptide family cut and secreted from the progranulin. Progranulin is also designated as proepithelin or a PC cell-derived growth factor.

GDF-15 (growth differentiation factor 15) is a protein, also known as macrophage inhibitory cytokine 1 (MIC1), belonging to the transforming growth factor beta (TGF-β) superfamily playing a role of regulating the inflammatory pathway and the cell death pathway in wound tissues and disease process.

Examples of cytokines except for the aforementioned cytokines secreted by the mesenchymal stem cells of the present invention include osteoprotegerin and MMP1. The mesenchymal stem cells of the present invention preferably secrete osteoprotegerin and/or MMP1, and further preferably both of these cytokines.

As was previously described in the section on gene expression, osteoprotegerin (TNFRSF11B) is a decoy receptor of an osteoclast differentiation factor (RANKL) and inhibits activation of NF-κB signaling mediated by RANK. It is produced by osteoblasts, fibroblasts and hepatocytes, and inhibits differentiation of osteoclast progenitor cells into osteoclasts. The local administration of osteoprotegerin has been reported to promote osteogenesis, while conversely to induce osteoporosis as a result of a knockdown.

As was previously described in the section on gene expression, MMP1 (matrix metalloproteinase 1) is an interstitial collagenase involved in tissue destruction and tissue reconstruction by specifically cleaving the helix sites of type I, type II, type III and type IV collagen. The lower secretion of MMP1 in the mesenchymal stem cells expressing the specific marker of the present invention compared to the specific marker negative cells is expected to be effective in repairing tissues at sites of inflammation and damage.

Furthermore, the secreted amount of cytokine (or concentration in culture supernatant) can be measured according to a method known among persons with ordinary skill in the art. An example of such a method is ELISA.

(Differentiation Directionality)

The mesenchymal stem cells expressing the specific marker of the present invention have capacity to differentiate into bone, the adipose tissue and cartilage. Each of these differentiation capacities can be determined by culturing a population of the aforementioned mesenchymal stem cells under conditions that induce differentiation that are known among persons with ordinary skill in the art.

A conventionally used induction method can be used to induce differentiation to osteocytes, and although there are no particular limitations thereon, differentiation can typically be induced according to a method such as the following. After having cultured the mesenchymal stem cells of the present invention for several days, the cells are suspended and seeded in a differentiation culture broth containing FBS or other serums, dexamethasone, (3-glycerol phosphate and ascorbic acid-2-phosphate. Alternatively, a commercially available osteocyte differentiation medium may be used for the aforementioned differentiation culture broth. Examples of such commercially available bone differentiation media include Osteolife Complete Osteogenesis Medium (Lifeline Corp., LM-0023) and Mesenchymal Stem Cell Osteogenic Differentiation Medium (Takara Bio Inc., D12109). When culturing to induce bone differentiation, the medium is replaced about 24 to 72 hours after seeding the cells for differentiation culturing, and thereafter, the medium is replaced every 3 to 4 days until the cells are cultured for about 2 weeks to 1 month.

A conventionally used induction method can be used to induce differentiation into adipocytes, and although there no particular limitations thereon, the method typically consists of suspension-culturing the cells for several days in a culture broth containing retinoic acid, followed by culturing them in a culture broth containing insulin and triiodothyronine (T3). In addition, culture conditions conventionally used for culturing this type of cell can be used, and there are no particular limitations on, for example, the type of medium, the contents of the composition, the concentration of the composition and the incubation temperature. In addition, although a period of not more than 21 days is typically preferable as the incubation period, culturing can be continued for about 30 days to 40 days. More specifically, adipocytes can be induced according to the method described below. After having cultured the mesenchymal stem cells of the present invention for several days, the cells are seeded at the recommended cell density as stated in the Kurabo protocol by suspending in adipocyte differentiation medium. Examples of the aforementioned differentiation medium include human mesenchymal stem cell adipocyte differentiation media such as AdipoLife DfKt-1 (Lifeline Corp., LL-0050), AdipoLife DfKt-2 (Lifeline Corp., LL-0059) or Mesenchymal Stem Cell Adipogenic Differentiation Medium (Takara Bio Inc., D12107). When culturing for differentiation into adipocytes, the medium is replaced about 24 to 72 hours after seeding the cells for differentiation culturing, and thereafter, the medium is replaced every 3 to 4 days until the cells are cultured for about 2 weeks to 1 month.

A conventionally used induction method can be used to induce differentiation into chondrocytes, and although there no particular limitations thereon, the method typically consists of mixing the mesenchymal stem cells of the present invention with collagen gel and the like to form a gel followed by culturing them in DMEM medium after adding differentiation culture broth thereto containing dexamethasone, ascorbic acid-2-phosphate, sodium pyruvate, transforming growth factor β3 (TGF-β3) and ITS Plus Premix (mixture of insulin, transferrin and selenite). The cells are cultured for about 3 weeks while replacing the medium about two to three times a week. More specifically, chondrocytes can be induced according to the method described below. After having cultured the mesenchymal stem cells of the present invention for several days, the cells are seeded using the micro mass method at the recommended cell density as stated in the Kurabo protocol by suspending them in chondrocyte differentiation medium. Examples of the aforementioned chondrocyte differentiation medium include ChondroLife Complete Chondrogenesis Medium (Lifeline Corp., LM-0023) and Mesenchymal Stem Cell Chondrogenic Differentiation Medium w/o Inducers (Takara Bio Inc., D12110). The medium is replaced every 3 to 4 days thereafter until the cells are cultured for about 2 weeks to 1 month.

The type of cells that the cells obtained according to the aforementioned differentiation induction methods differentiated into can be ascertained by using a biochemical approach or morphological observation. For example, the type of the differentiated cells can be ascertained by various identification methods such as observation under a microscope, various cell staining methods, northern blotting using hybridization or RT-PCR.

Although adipocytes, osteocytes and chondrocytes are difficult to be identified based on cell morphology, the presence of adipocytes can be confirmed by staining for intracellular lipids (which can be stained red with Oil Red O stain, for example). In addition, the presence of osteocytes can be confirmed by staining the cells with Alizarin red. Furthermore, the presence of chondrocytes can be confirmed by staining with Alcian blue, Safranin O or Toluidine blue.

The mesenchymal stem cells of the present invention have the capacity to differentiate into adipocytes, osteocytes and chondrocytes, and the capacity to differentiate into adipocytes and osteocytes in particular is remarkably improved in comparison with mesenchymal stem cell populations cultured with conventional media.

[Preparation of Mesenchymal Stem Cells Expressing Specific Marker]

Although there are no particular limitations on the method used to prepare the mesenchymal stem cells expressing the specific marker, the cells can be prepared according to, for example, the method indicated below. Namely, mesenchymal stem cells are isolated from umbilical cord, adipose tissue or bone marrow and the like and cultured in accordance with a method known among persons with ordinary skill in the art, and specific marker-positive cells can be obtained by isolation with a cell sorter or magnetic beads and the like using an antibody that specifically binds with the specific marker (such as an anti-CD201 antibody, an anti-CD46 antibody, an anti-CD56 antibody, an anti-CD147 antibody and/or an anti-CD165 antibody). Preferably 70% or more of the cell population obtained by such a method is specific marker-positive, more preferably 80% or more is specific marker-positive, even more preferably 90% or more is specific marker-positive, still more preferably 95% or more is specific marker-positive, and most preferably 99% or more is specific marker-positive. The following provides a detailed explanation of a method for preparing the mesenchymal stem cells expressing the specific marker.

A method such as the following can be used to prepare mesenchymal stem cells expressing the specific marker of the present invention. Mesenchymal stem cells can be acquired and cultured by a method that includes the steps of (A) treating tissues containing mesenchymal stem cells with enzymes, (B) carrying out adhesion-culturing by suspending the cell obtained according to the aforementioned treatment in a suitable culture medium, (C) removing the suspended cells, and (D) subculturing the mesenchymal stem cells. The following provides a detailed explanation of each step.

In step (A) for treating tissues containing mesenchymal stem cells with enzymes or the like, the tissues containing mesenchymal stem cells such as the umbilical cord, adipose or bone marrow and the like are washed by a method employing agitation and precipitation using physiological saline (phosphate-buffer saline (PBS), for example) (including a method employing centrifugation). The contaminants contained in the aforementioned tissues can be removed from the tissues by this procedure. When the remaining cells are present in the form of aggregates of various sizes, the washed cell aggregates are preferably treated with enzymes that weaken or destroy the bonds between the cells (such as collagenase, dispase or trypsin) in order to dissociate the cells while minimizing the damage caused thereto. Although the amount of the enzyme used and the duration of the enzyme treatment vary depending on the conditions, this treatment can be carried out within the scope of common general technical knowledge in the art. Although the cell aggregates can also be broken up by other treatment methods such as mechanical agitation, ultrasonic energy or thermal energy either in place of or in combination with this enzyme treatment, treating the cells with enzymes alone is preferable in order to minimize cell damage. In the case of using enzymes, the enzymes should preferably be deactivated using a medium or the like following the enzyme treatment so that harmful effects on the cells are minimized.

The cell suspension obtained according to the aforementioned process contains a slurry, a suspension of aggregated cells or various contaminant cells such as erythrocytes, smooth muscle cells, endothelial cells or fibroblasts. Thus, although the aggregated cells and these contaminant cells may be subsequently separated and removed, such steps may be omitted since removal is possible by a suspended cell removal step that will be described later. In the case of separating and removing contaminant cells, this can be achieved by centrifugation that forcibly separates the cells into supernatant and precipitate. The resulting precipitate containing contaminant cells is suspended in a suitable solvent. Although the suspended cells may contain erythrocytes, since erythrocytes are excluded by selecting the erythrocytes by being adhered to a solid surface, a step that is to be described later, a lysing step is not necessarily required. A method known in the art such as incubation in a hypertonic or hypotonic medium obtained by lysing with ammonium chloride can be used to selectively lyse erythrocytes. After lysing, the lysed fragments may be separated from the desired cells by, for example, filtration, centrifugal sedimentation or density fractionation.

Next, in step (B) for carrying out adhesion-culturing by suspending the cells obtained according to the aforementioned enzyme treatment in a suitable culture medium, the suspended cells may be washed once or more continuously, centrifuged, and re-suspended in a culture medium in order to increase the purity of the mesenchymal stem cells. In addition, the cells may be separated on the basis of a cell surface marker profile or on the basis of cell size and granularity. In this step, only those cells expressing the specific marker protein may be selectively separated by a cell sorter or an immunochemical technique using magnetic beads and the like.

There are no particular limitations on the medium used for re-suspending the cells provided that it enables mesenchymal stem cells to be cultured, and for example, it can be prepared by adding a serum and/or a serum substitute to a basal medium for culturing animal cells. Alternatively, commercially available media suitable for culturing mesenchymal stem cells may be used as the medium. Furthermore, in the present invention, a medium containing minimum biological raw materials (such as a serum-free medium) is preferably used in order to allow the mesenchymal stem cells or culture supernatant thereof to be used to treat animal (including human) diseases. A medium containing no components derived from different species (such as a Xeno-Free medium) is particularly preferable.

The composition of the aforementioned basal medium can be appropriately selected according to the type of cells to be cultured. Examples thereof include minimum essential medium (MEM) such as Eagle's medium, Dulbecco's modified Eagle's medium (DMEM), minimum essential medium α (MEM-α), mesenchymal stem cell basal medium (MSCBM), Ham's F-12 and F-10 medium, DMEM/F12 medium, William's medium E, RPMI-1640 medium, MCDB medium, 199 medium, Fisher's medium, Iscove's modified Dulbecco's medium (IMDM) and McCoy's modified medium.

Examples of serum include, but are not limited to, human serum, fetal bovine serum (FBS), bovine serum, bovine calf serum, goat serum, horse serum, pig serum, sheep serum, rabbit serum and rat serum. In the case of using a serum, the serum may be added to a basal medium at 0.5% to 15% and preferably at 5% to 10%. Examples of serum substitutes added to the basal medium include albumin, transferrin, fatty acids, insulin, sodium selenite, collagen precursor, trace elements, 2-mercaptoethanol and 3'-thioglycerol.

Examples of substances added to the aforementioned basal medium include, but are not limited to, amino acids, inorganic salts, vitamins, growth factors, antibiotics, trace metals, stem cell differentiation inducers, antioxidants, carbon sources, salts, sugars, sugar precursors, plant-derived hydrolysates, surfactants, ammonia, lipids, hormones, buffers, indicators, nucleosides, nucleotides, butyric acid, organic matter, DMSO, plant-derived products, gene induction agents, intracellular pH adjusters, betaine, osmoprotectants and minerals. There are no limitations on the concentrations at which these substances are used, and concentrations that are used in ordinary mammalian cell media may be selected.

Examples of the aforementioned amino acids include glycine, L-alanine, L-arginine, L-asparagine, L-aspartic acid, L-cysteine, L-cystine, L-glutamic acid, L-glutamine, L-histidine, L-isoleucine, L-leucine, L-lysine, L-methionine, L-phenylalanine, L-proline, L-serine, L-threonine, L-tryptophan, L-tyrosine and L-valine.

Examples of the aforementioned inorganic salts include calcium chloride, copper sulfate, iron (II) nitrate, iron sulfate, magnesium chloride, magnesium sulfate, potassium chloride, sodium bicarbonate, sodium chloride, disodium hydrogen phosphate and sodium dihydrogen phosphate.

Examples of the aforementioned vitamins include choline, vitamin A, vitamin B1, vitamin B2, vitamin B3, vitamin B4, vitamin B5, vitamin B6, vitamin B7, vitamin B12, vitamin B13, vitamin B15, vitamin B17, vitamin Bh, vitamin Bt, vitamin Bx, vitamin C, vitamin D, vitamin E, vitamin F, vitamin K, vitamin M and vitamin P.

In addition, specific examples of substances that can be added to the basal medium include growth factors such as basic fibroblast growth factor (bFGF), endothelial growth factor (EGF), platelet-derived growth factor (PDGF), epidermal growth factor (EGF), insulin-like growth factor (IGF), transforming growth factor (TGF), nerve growth factor (NGF), brain-derived neurotrophic factor (BDNF), vascular endothelial growth factor (VEGF), granulocyte-colony stimulating factor (G-CSF), granulocyte-macrophage colony stimulating factor (GM-CSF), erythropoietin (EPO), thrombopoietin (TPO) or hepatocyte growth factor (HGF), antibiotics such as penicillin, streptomycin, neomycin sulfate, amphotericin B, blastocydine, chloramphenicol, amoxicillin, bacitracin, bleomycin, cephalosporin, chlortetracycline, zeocin or puromycin, carbon sources such as glucose, galactose, fructose or sucrose, trace metals such as magnesium, iron, zinc, calcium, potassium, sodium, copper, selenium, cobalt, tin, molybdenum, nickel or silicon, stem cell differentiation inducers such as β-glycerophosphoric acid, dexamethasone, rosiglitazone, isobutyl methylxanthine or 5-azacytidine, antioxidants such as 2-mercaptoethanol, catalase, superoxide dismutase or N-acetylcysteine, adenosine-5'-monophosphate, corticosterone, ethanolamine, insulin, reduced glutathione, lipoic acid, melatonin, hypoxanthine, phenol red, progesterone, putrescine, pyruvic acid, thymidine, triiodothyronine, transferrin and lactoferrin.

Examples of serum-free media preferable for the mesenchymal stem cells of the present invention include commercially available, serum-free media. Examples thereof include pre-prepared media for mesenchymal stem cells available from PromoCell GmbH, Lonza Group Ltd., Biological Industries Inc., Veritas Corp., R&D Systems Inc., Corning Inc. and Rohto Pharmaceutical Co., Ltd.

Next, the mesenchymal stem cells are cultured at a suitable cell density and under suitable culturing conditions using a suitable medium as described above on a solid surface such as a culture vessel without being differentiated. There are no limitations on the shape of the culture vessel having a solid surface, but a Petri dish or flask is used preferably. There are no limitations on the culturing conditions of the mesenchymal stem cells of the present invention provided that the conditions are suitable for the type of mesenchymal stem cells to be cultured, and conventional methods are used. Normally, culturing is carried out at a temperature of 30° C. to 37° C. in an environment containing 2% to 7% $CO_2$ and 5% to 21% $O_2$.

In step (C) for removing suspended cells, the suspended cells and the cell fragments not adhered to the solid surface of the culture vessel are removed, and the adhered cells are washed using physiological saline (such as phosphate-buffered saline (PBS)). In the present invention, cells ultimately remaining adhered to the solid surface of the culture vessel can be selected for use as the cell population of the mesenchymal stem cells.

Next, the step (D) for subculturing the mesenchymal stem cells is carried out. There are no limitations on the culturing method provided that it is suitable for the type of cell to be cultured, and conventional methods are used Normally, culturing is carried out at a temperature of 30° C. to 37° C. in an environment containing 2% to 7% $CO_2$ and 5% to 21% $O_2$. There are either no limitations on the timing and the method used to subculture the mesenchymal stem cells provided that they are suitable for the type of cells to be cultured, and conventional methods are used while the status of the mesenchymal stem cells are being monitored. The same medium as the one used in step (B) can be used for culturing. Furthermore, culturing may be carried out using a serum-free medium throughout the entire cell incubation period.

The preparation method of the present invention preferably further includes a step (E) for selectively separating, from the mesenchymal stem cells obtained by culturing in the aforementioned step (D), merely cells expressing the specific marker protein with a cell sorter or by an immunological technique using magnetic beads or the like. Through the step (E), the mesenchymal stem cells expressing the specific marker can be efficiently obtained.

The thus obtained mesenchymal stem cells may be prepared for treatment by suspending in an infusion or the like to be used for a patient, or may be cryopreserved once. The cryopreservation can be performed by a method conventionally known among persons with ordinary skill in the art. When the cryopreserved cells are to be used for a patient, they may be administered directly after thawing, or may be administered after suspending in an infusion or the like.

[Pharmaceutical Composition]

The pharmaceutical composition of the present invention is characterized by containing the mesenchymal stem cells expressing the specific marker and/or a culture supernatant thereof. As described above, the mesenchymal stem cells expressing the specific marker of the present invention have the superior properties of demonstrating anti-inflammatory actions such as inhibitory action on the production of inflammatory cytokines such as IL-6, barrier function enhancing action and anti-fibrotic action. In addition, the mesenchymal stem cells are capable of efficiently differentiating into cells having a target function under differentiation conditions while simultaneously maintaining an undifferentiated state. The pharmaceutical composition of the present invention that contains such mesenchymal stem cells expressing the specific marker and/or the culture supernatant thereof demonstrates excellent therapeutic effects against various diseases. The pharmaceutical composition of the present invention may also contain other components in addition to the mesenchymal stem cells expressing the specific marker and/or the culture supernatant thereof within a range that does not impair the effects of the present invention.

The pharmaceutical composition of the present invention contains a mesenchymal stem cell population and/or a culture supernatant thereof, and a part or the whole of the mesenchymal stem cell population corresponds to the mesenchymal stem cells expressing the specific marker. The properties and the like of the mesenchymal stem cells expressing the specific marker have been described in the item on the mesenchymal stem cells expressing the specific marker. The ratio of the mesenchymal stem cells expressing the specific marker in the mesenchymal stem cell population contained in the pharmaceutical composition of the present invention is preferably as high as possible. The aforementioned ratio is preferably 50% or more, more preferably 70% or more, even more preferably 90% or more, particularly preferably 95% or more, and most preferably 99% or more.

[Preparation of Pharmaceutical Composition]

The present invention also includes a method for preparing a pharmaceutical composition used to treat or prevent disease that includes a step for inducing, concentrating or isolating and sorting mesenchymal stem cells expressing the specific marker. Examples of the aforementioned disease include diseases selected from the group consisting of cancer, precancerous symptoms, inflammatory diseases, immune diseases, neurodegenerative diseases, metabolic diseases, cardiovascular diseases, heart diseases, bone diseases, gastrointestinal diseases, lung diseases, liver diseases and oral diseases.

The method for preparing a pharmaceutical composition of the present invention includes a step for inducing, concentrating or isolating and sorting mesenchymal stem cells expressing the specific marker. There are no particular limitations on the method used in the aforementioned step for inducing mesenchymal stem cells expressing the specific marker provided it is a method capable of inducing or enhancing expression of the specific marker in mesenchymal stem cells.

In addition, examples of methods used in the step for concentrating, isolating and sorting mesenchymal stem cells expressing the specific marker include methods using a cell sorter or magnetic beads by using antibody that specifically recognizes the specific marker. According to these methods, mesenchymal stem cells expressing the specific marker protein on the cell surface thereof can be selectively concentrated, isolated and sorted.

There are no particular limitations on the culture supernatant of the mesenchymal stem cells of the present invention provided that it is a culture supernatant obtained by culturing the mesenchymal stem cells, and is preferably a culture supernatant obtained by the culturing method described in detail in the aforementioned item of "Preparation of Mesenchymal Stem Cells Expressing Specific Marker". In other words, it is a culture supernatant obtained by first culturing mesenchymal stem cells, and then culturing the mesenchymal stem cells in a replacement medium.

Furthermore, although a culture supernatant of the mesenchymal stem cells of the present invention refers to that from which mesenchymal stem cells have been removed from a culture broth (culture broth following culturing) obtained by culturing the mesenchymal stem cells in a culture broth that allows the mesenchymal stem cells to grow or survive under conditions that allow mesenchymal stem cells to grow or survive, it also includes that from which it also includes that from which at least a portion of components not contributing to the effects of the present invention, such as residual medium components (components of the culture broth prior to culturing remaining in the culture broth after culturing) or moisture present in the culture broth, have been further removed from the culture supernatant, and for the sake of convenience, includes the culture supernatant of the mesenchymal stem cells in the present description. Furthermore, from the viewpoint of convenience, that from which mesenchymal stem cells have been removed from a culture broth following culturing is preferably used as it is as a culture supernatant.

The culture supernatant of the mesenchymal stem cells of the present invention contains Crossveinless-2 and Ectodysplasin-A2. The culture supernatant preferably further contains activin A, Dkk-3, decorin, HGF, Dkk-1, progranulin, GDF-15, angiopoietin-1, CCL28, latent TGF-β binding protein 1, GDF1 or VEGF-C, BTC, Nidogen-1, GLO-1, sgp130, Chordin-Like 2 or EMAP-II. It more preferably further contains osteoprotegerin or MMP-1. The culture supernatant of the mesenchymal stem cells of the present invention further preferably contains all of these cytokines.

In addition to the mesenchymal stem cells expressing the specific marker acquired according to the aforementioned step for inducing, concentrating or isolating and sorting mesenchymal stem cells expressing the specific marker, the pharmaceutical composition of the present invention may also contain the specific marker negative mesenchymal stem cells as well as other cells within a range that does not impair the effects of the present invention, and pharmaceutically acceptable carriers and additives may be contained corresponding the application and form thereof in accordance with routine methods. Examples of such carriers and additives include, but are not limited to, isotonic agents, thickeners, sugars, sugar-alcohols, antiseptics (preservatives), disinfectants or antimicrobial agents, pH adjusters, stabilizers, chelating agents, oily bases, gel bases, surfactants, suspending agents, binders, excipients, lubricants, disintegrating agents, foaming agents, fluidizing agents, dispersants, emulsifiers, buffers, solubilizing agents, antioxidants, sweeteners, sour agents, colorants, flavoring agents, fragrances and fresheners. The following indicates examples of carriers and additives used as typical components.

[Applications of Mesenchymal Stem Cells Expressing Specific Marker and Pharmaceutical Composition Containing Same of Present Invention]

(Action of Enhancing Barrier Function of Culture Supernatant)

A culture supernatant of the mesenchymal stem cells expressing the specific marker of the present invention demonstrates an effect that results in superior enhancement of the barrier function of cells in comparison with a culture supernatant of conventional specific marker negative mesenchymal stem cells. Namely, since a culture supernatant of the mesenchymal stem cells expressing the specific marker of the present invention demonstrates a remarkable effect that enables recovery of the barrier function of cells that have been damaged by inflammation, the mesenchymal stem cells expressing the specific marker and pharmaceutical composition containing the same of the present invention can be preferably used to treat diseases associated with inflammation. In addition, the mesenchymal stem cells expressing the specific marker or culture supernatant thereof can also be used in cosmetic compositions or food compositions and the like.

(Anti-Inflammatory Action)

The mesenchymal stem cells expressing the specific marker of the present invention have an effect that inhibits the production of inflammatory cytokines by macrophages during inflammation. This effect is significantly more potent in comparison with conventional specific marker negative mesenchymal stem cells. Consequently, the mesenchymal stem cells expressing the specific marker and pharmaceutical composition containing the same of the present invention can be preferably used to treat diseases associated with inflammation. In addition, the mesenchymal stem cells expressing the specific marker or culture supernatant thereof can also be used in cosmetic compositions or food compositions and the like.

(Anti-Fibrotic Effect on Vascular Endothelial Cells)

The mesenchymal stem cells expressing the specific marker of the present invention act on human vascular endothelial cells (HUVEC), and demonstrate an effect of inhibiting expression of TGFβ and COL3A1, that is, genes relating to fibrosis. Accordingly, the mesenchymal stem cells of the present invention can be said to be effective for diseases such as arteriosclerosis in which the fibrosis of vascular endothelial cells is involved.

(Anti-Inflammatory Effect and Anti-Fibrotic Effect on Lung Epithelial Cells)

The culture supernatant of the mesenchymal stem cells of the present invention acts on human lung epithelial carcinoma cells (such as A549), and demonstrates an effect of inhibiting expression of LITAF, that is, a gene relating to inflammation, and COL1A1, that is, a gene relating to fibrosis. Accordingly, the mesenchymal stem cells of the present invention can be said to be effective for diseases, such as lung/respiratory inflammation and chronic obstructive pulmonary disease (COPD), in which inflammation and fibrosis of lung epithelial cells are involved. Besides, the effect on lung cancer can be expected.

(Anti-Inflammatory Effect and Anti-Fibrotic Effect on Hepatic Stellate Cells)

The culture supernatant of the mesenchymal stem cells of the present invention acts on human hepatic stellate cells (hHsteC), and demonstrates an effect of inhibiting expression of IL-1β, LITAF and IL-8, that is, genes relating to inflammation, and COL1A1, that is, a gene relating to fibrosis. Accordingly, the mesenchymal stem cells of the present invention can be said to be effective for diseases, such as lung/respiratory inflammation and chronic obstructive pulmonary disease (COPD), in which inflammation and fibrosis of hepatic stellate cells are involved.

(Anti-Inflammatory Effect and Anti-Fibrotic Effect on Cardiac Myocytes)

The culture supernatant of the mesenchymal stem cells of the present invention acts on human cardiac myocytes (hCM), and demonstrates an effect of inhibiting expression of LITAF and TNFα, that is, genes relating to inflammation, and TGFβ, that is, a gene relating to fibrosis. Accordingly, the mesenchymal stem cells of the present invention can be said to be effective for diseases, such as myocarditis and cardiac hypertrophy, in which inflammation and fibrosis of cardiac myocytes are involved.

(Anti-Inflammatory Effect and Anti-Fibrotic Effect on Gingival Fibroblasts)

The culture supernatant of the mesenchymal stem cells of the present invention acts on human gingival fibroblasts (hGF), and demonstrates effects of inhibiting expression of LITAF, that is, a gene relating to inflammation, and enhancing expression of COL1A1 and COL3A1, that is, genes relating to fibrosis. With respect to hGF, it is regarded that fibrosis is preferably promoted to improve periodontal disease. In other words, when the expression of COL1A1 and COL3A1 is enhanced, it can be determined that an effect of improving periodontal disease is obtained. Accordingly, the mesenchymal stem cells of the present invention can be said to be effective for diseases such as periodontal disease in which gingival fibroblasts are involved.

Examples of diseases for which the mesenchymal stem cells expressing the specific marker of the present invention and the pharmaceutical composition containing the same can be used as a pharmaceutical include cancer, precancerous symptoms, inflammatory diseases, immune diseases, neurodegenerative diseases, metabolic diseases, cardiovascular diseases, heart diseases, bone diseases, gastrointestinal diseases, lung diseases, liver diseases, kidney diseases and oral diseases. Specific examples include lung cancer, myocarditis, cardiac hypertrophy, arteriosclerosis, phlebitis, lung/respiratory inflammation, bronchial asthma, chronic obstructive pulmonary disease (COPD), hepatitis, hepatic fibrosis, liver cirrhosis, periodontal disease, cartilage degradation, rheumatoid arthritis, psoriatic arthritis, spondylarthritis, osteoarthrosis, gout, psoriasis, multiple sclerosis, amyotrophic lateral sclerosis, Alzheimer's disease, Parkinson's disease, congestive heart failure, stroke, aortic valve stenosis, kidney failure, lupus, pancreatitis, allergies, fibrosis, anemia, atherosclerosis, restenosis, complications associated with chemotherapy and/or radiotherapy, type I diabetes, type II diabetes, autoimmune hepatitis, hepatitis C, primary biliary cirrhosis, primary sclerosing cholangitis, fulminant hepatitis, celiac disease, non-specific colitis, allergic conjunctivitis, diabetic retinopathy, Sjogren's syndrome, uveitis allergic rhinitis, asthma, asbestosis, silicosis, chronic granulomatous inflammation, alveolar fibrosis, sarcoidosis, glomerular nephritis, vasculitis, dermatitis, HIV-related cachexia, cerebral malaria, ankylosing spondylitis, leprosy, pulmonary fibrosis, fibromyalgia, esophageal cancer, gastroesophageal reflux, Barrett's esophagus, gastric cancer, duodenal cancer, small intestine cancer, appendix cancer, large bowel cancer, colon cancer, rectal cancer, anal cancer, pancreatic cancer, liver cancer, gallbladder cancer, spleen cancer, renal cancer, bladder cancer, prostate cancer, testicular cancer, uterine cancer, ovarian cancer, breast cancer and thyroid cancer.

Among these diseases, as the diseases for which the mesenchymal stem cells of the present invention or the pharmaceutical composition containing the same can be used as a pharmaceutical, cancer, precancerous symptoms, inflammatory diseases, cardiovascular diseases, heart diseases, lung diseases, liver diseases and oral diseases are preferred, and more specifically, lung cancer, myocarditis, cardiac hypertrophy, arteriosclerosis, phlebitis, lung/respiratory inflammation, bronchial asthma, chronic obstructive pulmonary disease (COPD), hepatitis, hepatic fibrosis, liver cirrhosis and periodontal disease are preferred.

Although there are no particular limitations thereon, examples of administration methods in the case of using the pharmaceutical composition of the present invention as a pharmaceutical preferably include intravascular administration (and preferably intravenous administration), intraperitoneal administration, intestinal administration and subcutaneous administration, with intravascular administration being more preferable.

Although the dosage (dose) of the pharmaceutical composition of the present invention can be varied according to the status of the patient (such as body weight, age, symptoms or general condition) and the drug form of the pharmaceutical composition of the present invention, from the viewpoint of demonstrating adequate preventive or therapeutic effects, a high dosage is preferable, while on the other hand, from the viewpoint of inhibiting adverse reactions, a low dosage tends to be preferable. Normally, in the case of administration to an adult, the dosage in terms of the number of cells is $5 \times 10^2$ to $1 \times 10^{12}$ cells/administration, preferably $1 \times 10^4$ to $1 \times 10^{11}$ cells/administration, and more preferably $1 \times 10^5$ to $1 \times 10^{10}$ cells/administration. Furthermore, this dosage may be administered in a single dose, may be administered in multiple doses, or may be divided into a plurality of administrations. In addition, normally in the case of administration to an adult, the dosage in terms of the number of cells per body weight is $1 \times 10$ to $5 \times 10^{10}$ cells/kg, preferably $1 \times 10^2$ to $5 \times 10^9$ cells/kg, and more preferably $1 \times 10^3$ to $5 \times 10^8$ cells/kg. Furthermore, this dosage may be administered in a single dose, may be administered in multiple doses, or may be divided into a plurality of administrations.

The present invention includes a method for preventing or treating a disease that is characterized by the use of mesenchymal stem cells expressing the specific marker or a pharmaceutical composition containing mesenchymal stem cells expressing the specific marker. Examples of the aforementioned disease include cancer, precancerous symptoms, inflammatory diseases, immune diseases, neurodegenerative diseases, metabolic diseases, cardiovascular diseases, heart diseases, bone diseases, gastrointestinal diseases, lung diseases, liver diseases and oral diseases.

Examples

Although the following provides a detailed explanation of the present invention through examples thereof, the present invention is not limited to the following examples.

<Preparation of Mesenchymal Stem Cells Expressing Specific Marker>

After conditioning umbilical cord-derived mesenchymal stem cells (UC-MSC: Umbilical Cord-derived Mesenchymal Stem Cells Wharton's Jelly (HMSC-WJ), FC-0020, Lifeline Corp.), adipose-derived mesenchymal stem cells (AD-MSC: Adipose-derived Mesenchymal Stem Cells, FC-0034, Lifeline Corp.) or bone marrow-derived mesenchymal stem cells (BM-MSC: Bone-marrow-derived Mesenchymal Stem Cells, Lifeline Corp.) with a medium recommended by Lifeline Corp. (hereinafter also simply referred to as the "recommended medium") under conditions of 37° C. and 5% $CO_2$, culturing was continued by subculturing every 2 to 3 days. During the culturing process, after the cells were stained with an anti-CD201 antibody, an anti-CD46 antibody, an anti-CD56 antibody, an anti-CD147 antibody or an anti-CD165 antibody as necessary, cells positive for the respective antigens were selected using a cell sorter.

<Ascertainment and Analysis of Mesenchymal Stem Cells Expressing Specific Marker>

(FACS Analysis)

Figure 2:
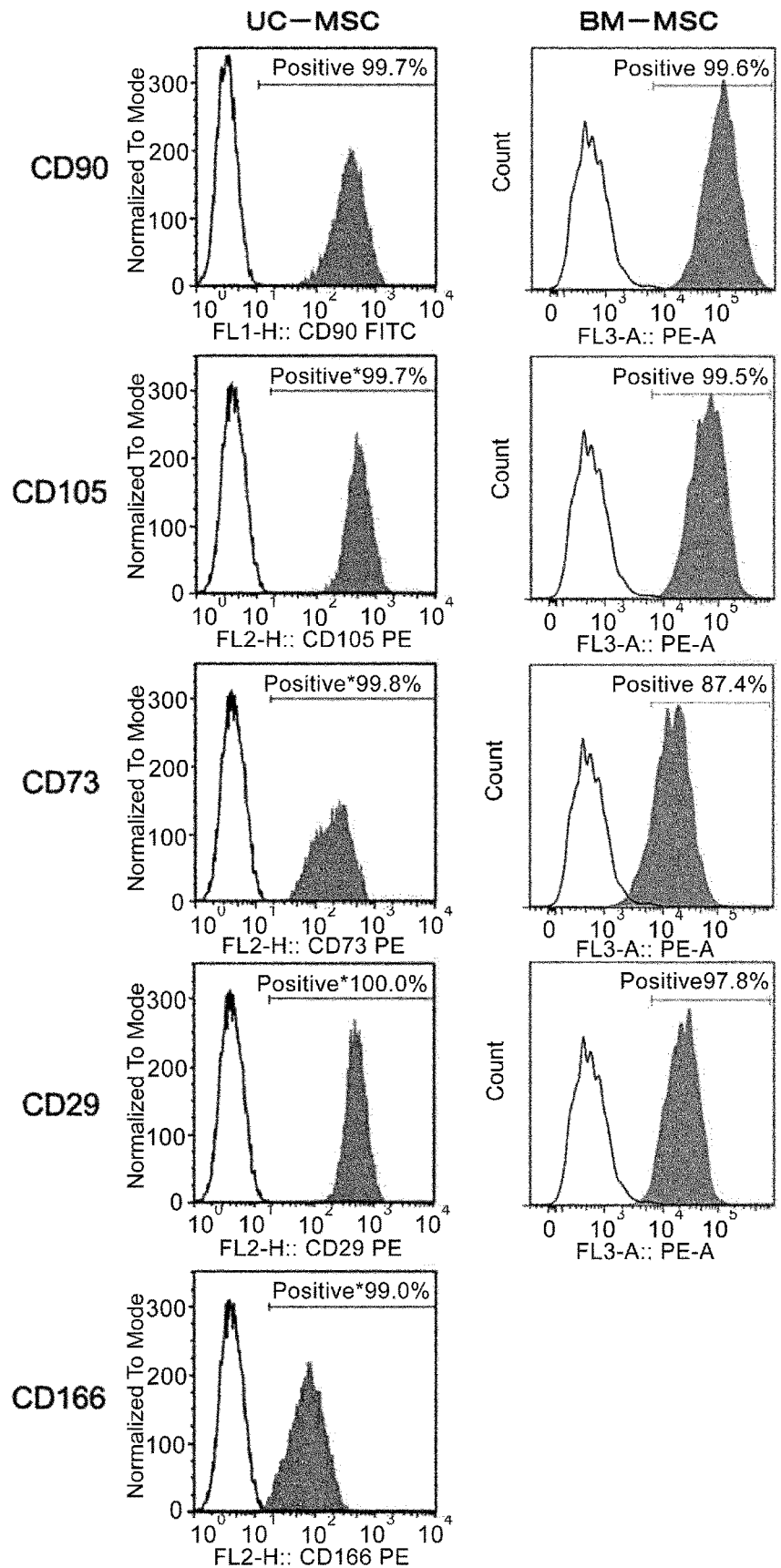
FIG. 2 depicts graphs indicating expression of cell surface markers by the mesenchymal stem cells of the present invention.

The mesenchymal stem cells (derived from umbilical cord, adipose and bone marrow) thus obtained were analyzed for the expression of CD201, CD46, CD56, CD147 and CD165 by FACS. The results are shown in FIG. 1. Besides, in order to ascertain an undifferentiated state of cells, expression of cell surface markers (CD29, CD73, CD90, 105 and/or CD166) was analyzed by the FACS. The results are shown in FIG. 2.

As shown in FIG. 1, the mesenchymal stem cells of the present invention derived from umbilical cord highly express CD201, CD46, CD56, CD147 and CD165. Besides, the mesenchymal stem cells of the present invention derived from adipose and derived from bone marrow highly express all of CD201, CD46, CD147 and CD165 but minimally express CD56. Furthermore, as shown in FIG. 2, the mesenchymal stem cells of the present invention derived from umbilical cord also express undifferentiation markers CD29, CD73, CD90, 105 and CD166. The mesenchymal stem cells derived from bone marrow express CD29, CD73, CD90 and 105.

(Intercellular Expression Level of miRNA in Specific Marker-Expressing Mesenchymal Stem Cells)

mRNA was prepared by a routine method from the specific marker-expressing mesenchymal stem cells derived from umbilical cord obtained as described above, and expression of miRNA in the cells was analyzed by using an miRNA array (miScript miRNA PCR array: MIHS-105Z and MIHS-117Z (Inflammatory Response, Autoimmunity and Fibrosis, Qiagen Inc.). The same test was carried out twice.

As a result of analyzing a total of about 150 types of miRNA, specific marker-expressing mesenchymal stem cells derived from umbilical cord were determined to express has-let-7e-5p, hsa-miR-132-3p, hsa-miR-196a-5p, hsa-miR-324-3p, hsa-miR-328-3p, hsa-miR-382-5p, hsa-let-7d-5p, hsa-miR-145-5p, hsa-miR-181a-5p, hsa-miR-29b-3p, hsa-miR-34a-5p, hsa-miR-199b-5p and hsa-miR-503-5p.

(Secretion of Cytokines into Culture Supernatant of Specific Marker-Expressing Mesenchymal Stem Cells Derived from Umbilical Cord)

The UC-MSC (from the eighth passage) of the present invention was seeded into a 100 mm plate at $1.5 \times 10^6$ cells/plate. The medium was replaced with a 0.2% FCS-containing DMEM/F-12 medium (2 ml/well) on the following day. After 48 hours, the culture supernatant was recovered.

The culture supernatant of the UC-MSC obtained as described above was concentrated ten times, and then analyzed by a known method using a cytokine array (Biotin Label-Based (L-Series) Human Antibody Array 493 (L-493) manufactured by RayBio). As a negative control, a 0.2% FCS-containing DMEM/F-12 medium having been placed in the same environment as the cell culturing environment for 48 hours was used. As a result of the analysis, the expression levels of Crossveinless-2, Ectodysplasin-A2, angiopoietin-1, activin A, Dkk-3, decorin, HGF, Dkk-1, progranulin and GDF-15 were increased by 32 times or more as compared with those in the negative control. Besides, the expression levels of CCL28, latent TGF-β binding protein 1, GDF1, VEGF-C, BTC, Nidogen-1, GLO-1, sgp130, Chordin-Like 2 and EMAP-II were increased by 20 to 30 times as compared with those in the negative control. Accordingly, the umbilical cord-derived mesenchymal stem cells were cells characterized by secretion of these cytokines in a large amount. The secreted amounts of these cytokines calculated on the assumption that the amount secreted in the negative control is 1 are shown in the following table.

TABLE 1

| Cytokine | Relative Expression Level |
|---|---|
| Activin A | 54.6 |
| Dkk-3 | 49.1 |
| Decorin | 45.6 |
| HGF | 41.6 |
| Crossveinless-2 | 41.1 |
| Dkk-1 | 38.7 |
| EDA-A2 | 36.4 |
| Progranulin | 35.9 |
| GDF-15 | 35.4 |
| Angiopoietin-1 | 32.4 |
| CCL28/VIC | 30.0 |
| Latent TGF-β Binding Protein 1 | 29.1 |
| GDF1 | 28.3 |
| VEGF-C | 27.7 |
| BTC | 25.4 |
| Nidogen-1 | 25.1 |
| GLO-1 | 23.8 |
| Sgp130 | 23.4 |
| Chordin-Like 2 | 22.9 |
| EMAP-II | 22.6 |

The specific marker-expressing umbilical cord-derived mesenchymal stem cells obtained as described above (the cells obtained with the medium replaced after being conditioned in the recommended medium) were re-seeded 8 days after, the medium was replaced with 0.2% FBS-containing DMEM/F12 on the following day, and the culture supernatant was recovered after two days (after 48 hours). The levels of decorin, osteoprotegerin and MMP1 in the recovered supernatant were measured by ELISA. The results are shown in the following Table 2.

TABLE 2

| | Pg/mL | |
|---|---|---|
| | Lot1 | Lot2 |
| Decorin | 10.7 | 17.8 |
| Osteoprotegerin | 84.4 | 67.1 |
| MMP-1 | 4800.1 | 1852.6 |

As shown in aforementioned Table 2, it was found that the culture supernatant of the specific marker-expressing umbilical cord-derived mesenchymal stem cells contained decorin, osteoprotegerin and MMP1.

(Effects of Culture Supernatant on Enhancing Barrier Function)

[Recovery of Culture Supernatant of Specific Marker-Expressing Umbilical Cord-Derived Mesenchymal Stem Cells]

The cells from the eighth passage of the specific marker-expressing umbilical cord-derived mesenchymal stem cells obtained as described above was seeded into a 6-well plate at $1.5 \times 10^5$ cells/well. The medium was replaced with an unconditioned medium (10% FCS-containing DMEM/F-12 medium, 2 ml/well) on the following day. After 24 hours, the culture supernatant (Sup-1) was recovered, and 2 ml aliquots of fresh medium were dispensed into each well and culturing was continued. The supernatant (Sup-2) was again recovered 24 hours later.

[Examination of Effect in Intestinal Barrier Model of Culture Supernatant of Specific Marker-Expressing Umbilical Cord-Derived Mesenchymal Stem Cells]

Figure 3:
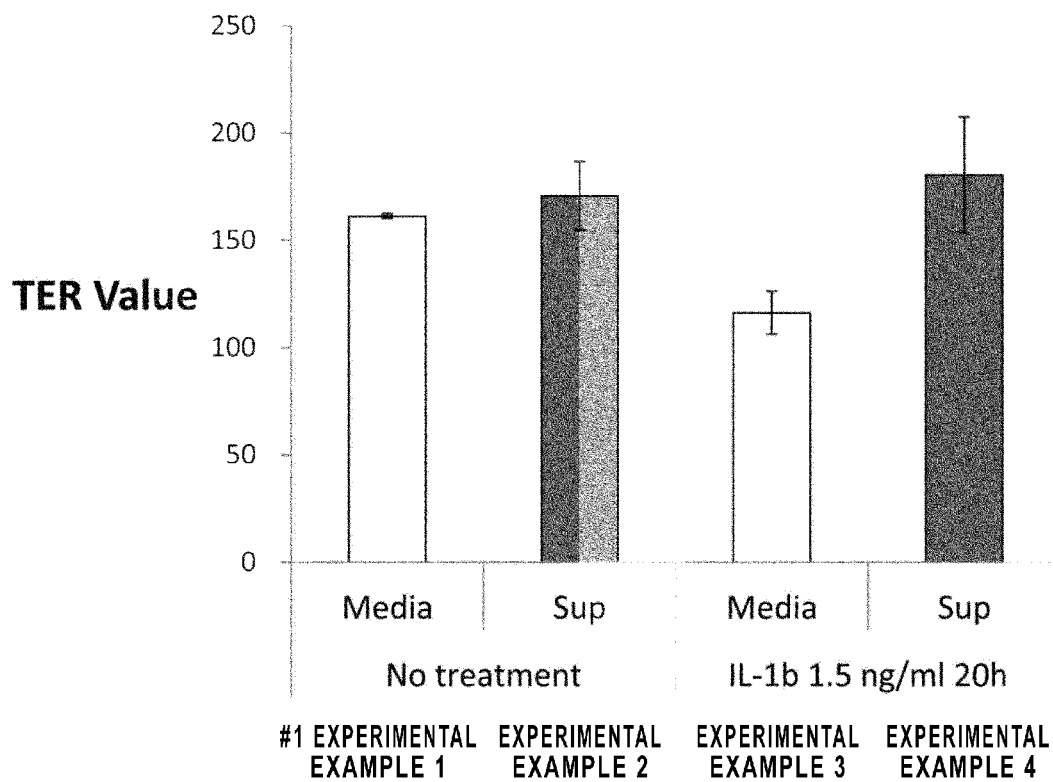
FIG. 3 is a bar graph indicating the barrier function enhancing activity of culture supernatants of the mesenchymal stem cells of the present invention.

Human colon cancer-derived cell line Caco-2 was subcultured in 10% FCS-containing DMEM medium and cells from the third passage were used in the present test. Caco-2 cells were seeded into a Transwell plate (Corning Costar Corp.) at $6 \times 10^4$ cells/well, and the media was removed on the following day after confirming that the cells had adhered to the Transwell. The aforementioned culture supernatant (Sup-1) of the specific marker-expressing mesenchymal stem cells derived from umbilical cord was diluted 10-fold with 10% FCS-containing DMEM medium and added to the Transwell plate. After removing the medium on the following day, the aforementioned culture supernatant (Sup-2) of the specific marker-expressing mesenchymal stem cells derived from umbilical cord was diluted 4-fold with 10% FCS-containing DMEM medium and added to the Transwell plate. Moreover, IL-1β was added at 1.5 ng/ml, and after additionally culturing for 20 hours, transepithelial electric resistance (TER) was measured. The number (absorbance) of Caco-2 cells cultured under the same conditions was measured with a cell growth assay kit (WST-8, Dojindo Laboratories, #343-07623), and the values obtained by dividing the resulting TER value by the number of cells (TER value) are shown in FIG. 3. Conditions of respective experimental examples are shown in the following Table 3.

TABLE 3

| | IL-1β Stimulation | Treatment |
|---|---|---|
| Experimental Example 1 | −(Vehicle) | Medium Alone |
| Experimental Example 2 | −(Vehicle) | UC-MSC Culture Supernatant |
| Experimental Example 3 | +(1.5 ng/ml) | Medium Alone |
| Experimental Example 4 | +(1.5 ng/ml) | UC-MSC Culture Supernatant |

As shown in FIG. 3, in comparison between Experimental Example 1 and Experimental Example 3, cell-to-cell barrier strength (a TER value) of the Caco-2 cells of Experimental Example 3 subjected to IL-1β treatment was lower than that of Experimental Example 1 not subjected to the IL-1β treatment, and it is thus understood that the cell-to-cell barrier strength (the TER value) of the Caco-2 cells was lowered through the IL-1β treatment. Besides, the addition of the culture supernatant of the specific marker-expressing umbilical cord-derived mesenchymal stem cells demonstrated a recovery up to a normal level of the cell-to-cell barrier strength (the TER value) of the Caco-2 cells thus lowered (Experimental Example 4). It was found based on these results that the culture supernatant of the specific marker-expressing umbilical cord-derived mesenchymal stem cells demonstrates an effect of recovering lowered cell-to-cell barrier strength of the Caco-2 cells, namely, a barrier function enhancing effect.

(Anti-Inflammatory Effect)

The specific marker-expressing umbilical cord-derived mesenchymal stem cells obtained as described above were used in the following test.

A medium was prepared by diluting a 0.5 mM DMSO solution of Calcein-AM staining reagent 1,000-fold with 10% FCS DMEM. The Calcein-AM-containing medium was added to mouse macrophage cell line Raw264.7, and after pre-culturing for 3 hours at 37° C. in 5% $CO_2$, the cells were seeded in a 48-well plate at $5\times10^5$ cells/well.

On the following day, the aforementioned specific marker-expressing mesenchymal stem cells derived from umbilical cord were added at $5\times10^3$ cells/well followed by initiation of co-culturing of the specific marker-expressing mesenchymal stem cells and Raw264.7 cells. LPS was added at 100 ng/mL 4 hours after the start of co-culturing. The culture supernatant was collected 17 to 18 hours later. The amount of IL-6 present in the culture supernatant was measured by ELISA (mIL-6 ELISA, R&D Duoset ELISA Kit, R&D Systems Inc., DY406-05). Furthermore, after recovering the culture supernatant, the number of cells corresponding to the amount of IL-6 was corrected by measuring the fluorescence value of Calcein-AM preliminarily taken up by the Raw264.7 cells and subtracting that value. The results are shown in FIG. 4.

Figure 4:
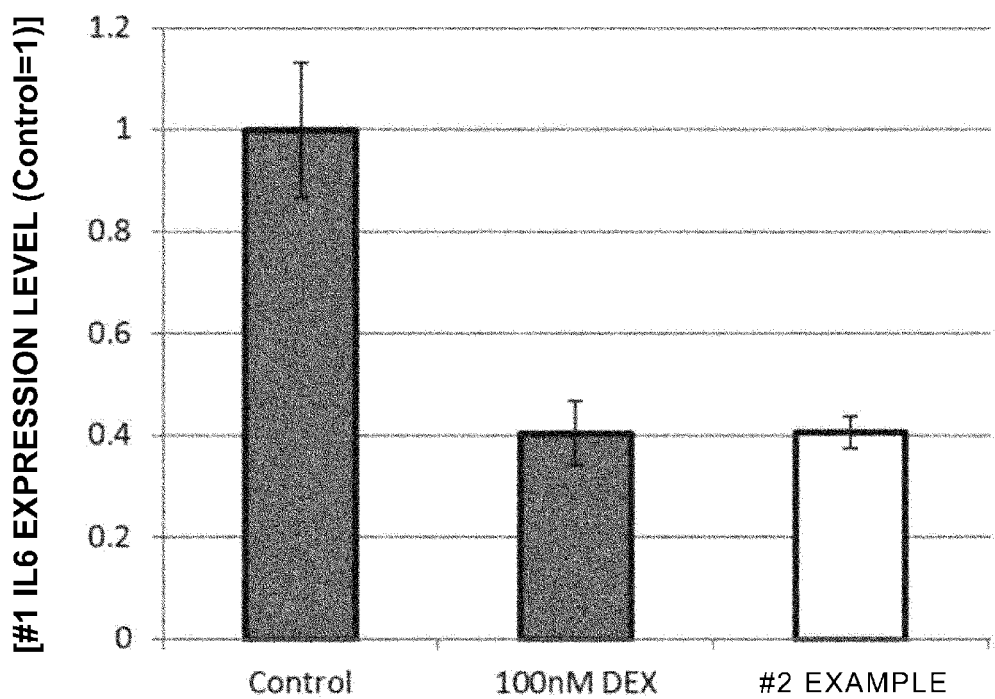
FIG. 4 is a bar graph indicating the inflammatory cytokine production inhibitory effect of the mesenchymal stem cells of the present invention.

As shown in FIG. 4, as a result of co-culturing with the specific marker-expressing mesenchymal stem cells derived from umbilical cord, production of inflammatory cytokine produced by mouse macrophage cell line Raw264.7 in the form of IL-6 was inhibited. Besides, the inhibitory effect thereof was substantially the same as that of dexamethasone (100 nM DEX) used as a positive control.

(Bone Differentiation Capacity)

The specific marker-expressing mesenchymal stem cells (derived from umbilical cord or adipose) obtained as described above were seeded into a 24-well plate (Cell Bind 3337, Corning Inc.) using an osteocyte differentiation medium (an osteocyte differentiation medium for human mesenchymal stem cells: Osteolife Complete Osteogenesis Medium, (Lifeline Corp., LM-0023)) at the cell density recommended in the Kurabo differentiation protocol. Culturing for inducing bone differentiation consisted of replacing the medium 48 hours after seeding in the differentiation medium followed by replacing the medium every 3 to 4 days thereafter for 28 days. The staining method consisted of washing the wells used for staining once with PBS starting on day 21 after seeding, followed by adding anhydrous ethanol and allowing to stand at room temperature for 30 minutes to fix the cells. The anhydrous ethanol was aspirated from the wells followed by allowing the wells to dry by allowing to stand undisturbed for about 30 minutes in a laminar flow cabinet. After adding 2% Alizarin red solution and allowing to stand undisturbed for 15 minutes at room temperature, the wells were washed twice with distilled water (DW) and allowed to dry. Photographs of the stained cells were captured using a microscope (Olympus IX70). It was found, as a result of Alizarin red staining, that the specific marker-expressing mesenchymal stem cells have the capacity to differentiate into bone.

(Adipose Differentiation Capacity)

The specific marker-expressing mesenchymal stem cells (derived from umbilical cord or adipose) obtained as described above were seeded in a 24-well plate (Cell Bind 3337, Corning Inc.) using differentiation medium (adipocyte differentiation medium for human mesenchymal stem cells: AdipoLife DfKt-1 (Lifeline Corp., LL-0050) or AdipoLife DfKt-2 (Lifeline Corp., LL-0059)) at the cell density recommended in the Kurabo differentiation protocol. Culturing for inducing adipose differentiation consisted of replacing the medium 48 hours after seeding for differentiation culturing followed by replacing the medium every 3 to 4 days thereafter for 28 days. The staining method consisted of washing the wells used for staining once with PBS starting on day 21 after seeding, followed by washing twice with 4% (v/v) paraformaldehyde-phosphate buffer solution so as to leave behind a small amount of the medium. The 4% (v/v) paraformaldehyde-phosphate buffer solution was added again followed by allowing to stand undisturbed for 20 minutes at room temperature. Subsequently, the wells were washed twice with distilled water (DW) so as to leave behind a small amount of the medium followed by washing once with 100% isopropanol. A stock solution of Oil Red O stain diluted to 60% with distilled water (DW) was then added followed by allowing to stand undisturbed for 30 minutes at 37° C. and then completely aspirating off the solution. 60% isopropanol was then added followed by the addition of distilled water after waiting for about 10 seconds. After washing twice with distilled water (DW), the cells were photographed with a microscope (Olympus IX70). Furthermore, DifFactor 3 (10 ml) was added to AdipoLife BM (100 ml) of the AdipoLife DfKt-2 medium to obtain a differentiation medium. It was found, as a result of Oil Red O staining, that the specific marker-expressing mesenchymal stem cells have the capacity to differentiate into adipocytes.

(Differentiation into Chondrocytes)

The specific marker-expressing mesenchymal stem cells (derived from umbilical cord or adipose) obtained as described above were seeded in a 24-well plate (3527, Corning Inc.) using differentiation medium (chondrocyte differentiation medium for human mesenchymal stem cells: ChondroLife Complete Chondrogenesis Medium (Lifeline Corp., LM-0023)) at the cell density recommended in the Kurabo differentiation protocol. Culturing for inducing cartilage differentiation consisted of seeding the cells according to the micromass method. More specifically, the recovered cells were concentrated in each maintenance medium to $1.6\times10^7$ cells/ml and dropped into a 24-well plate (3526, Corning Inc.) at 4 drops of 5 µl aliquots/well, and after allowing to stand undisturbed for 2 hours at 37° C. and 5% $CO_2$, chondrocyte differentiation medium was added at 500 µl/well. Subsequently, the medium was replaced every 3 days for 21 days. The staining method consisted of washing the wells used for staining once with PBS starting on day 21 after seeding, followed by adding 10% neutral-buffered formalin and allowing to stand for 30 minutes at room temperature to fix the cells. Subsequently, the wells were washed once with distilled water (DW) followed by the addition of 3% acetic acid and allowing to stand undisturbed for 1 minute. After adding Alcian Blue staining solution and allowing to stand undisturbed for 20 minutes at room temperature, the staining solution was aspirated and followed by the addition of 3% acetic acid and waiting for 3 minutes. Finally, the wells were washed twice with distilled water (DW) and photographed with a digital camera. As a result, it was found that the specific marker-expressing mesenchymal stem cells have the capacity to differentiate into chondrocytes.

(Fibrosis Inhibition Action of Culture Supernatant on Human Vascular Endothelial Cells)

[Recovery of Culture Supernatant of Specific Marker-Expressing Mesenchymal Stem Cells]

Cryopreserved cells of the aforementioned specific marker-expressing umbilical cord-derived mesenchymal stem cells (the cells obtained with the medium replaced after being conditioned in the recommended medium) were thawed to be cultured in the aforementioned recommended medium or a formulated medium (a medium obtained by adding L-glutamine, ascorbic acid, human recombinant albumin, bovine serum-derived fetuin, sodium bicarbonate, HEPES, lipid mix, ITSE mix, bFGF, progesterone, hydrocortisone, VO-OHPic, pifithrin-α, SB203580, lithium chloride and Y-27632 to DMEM/F-12 medium), and the resultant cells were re-seeded after 3 days. The medium was replaced with a DMEM/F12 medium containing 0.2% FBS and 1% AB (Antibiotic-Antimycotic (Gibco Corp.)), and the culture supernatant was recovered after 2 days (after 48 hours). The culture supernatant obtained from the cells cultured in the aforementioned recommended medium was designated as MSCsup1, and the culture supernatant obtained from the cells cultured in the aforementioned formulated medium was designated as MSCsup2. As a control medium to be used in the following experiment, a 0.2% FBS-containing DMEM/F-12 medium (containing no cells) having been placed in an incubator for 48 hours was used.

Figure 5:
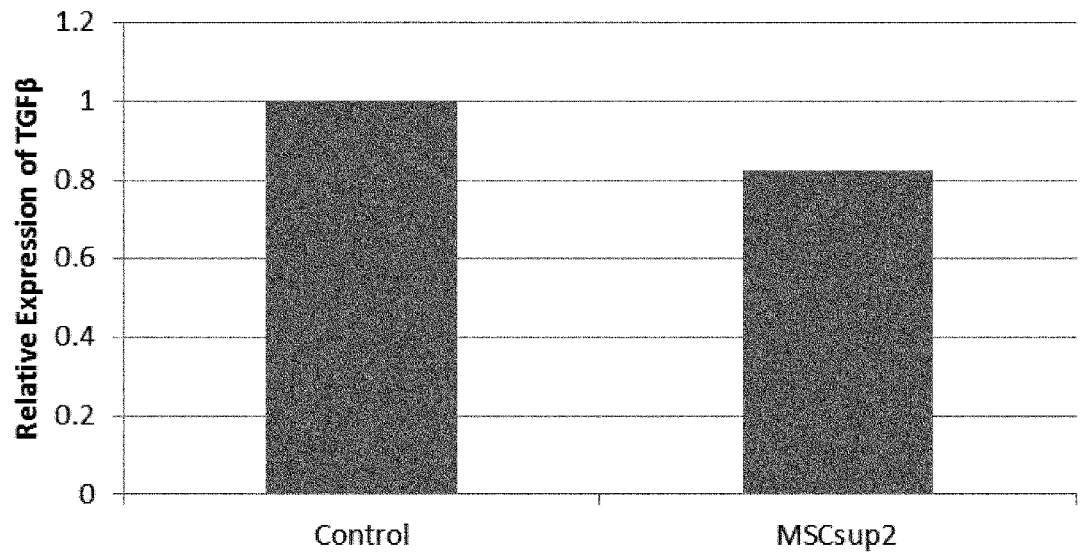
FIG. 5 is a bar graph indicating the anti-fibrotic effect on human vascular endothelial cells of culture supernatants of the mesenchymal stem cells of the present invention.
Figure 6:
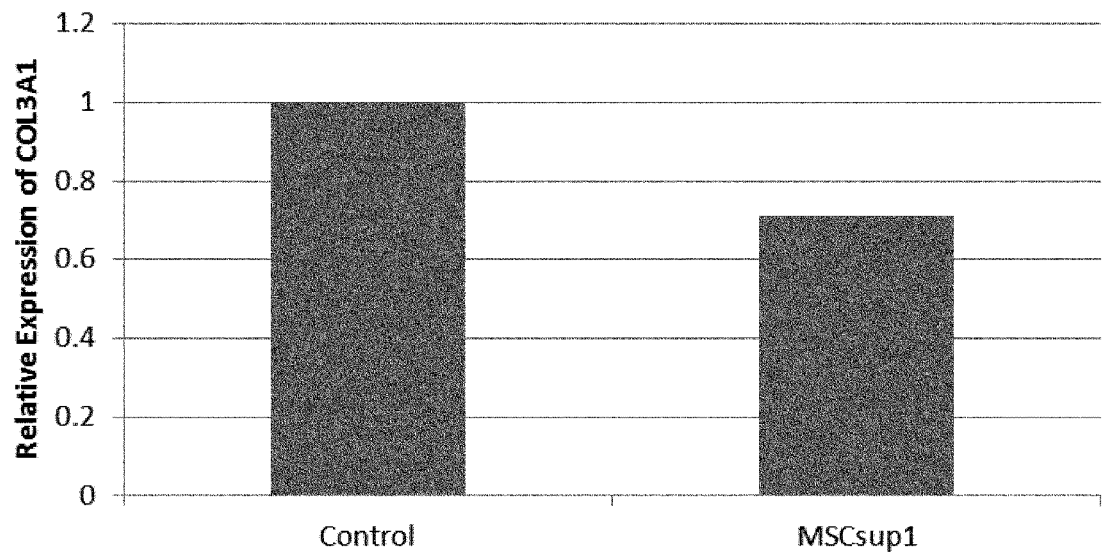
FIG. 6 is a bar graph indicating the anti-fibrotic effect on human vascular endothelial cells of culture supernatants of the mesenchymal stem cells of the present invention.

Human vascular endothelial cells HUVEC were seeded into a 6-well plate at $1\times10^5$ cells/well, the medium was removed on the following day, and the aforementioned culture supernatant (MSCsup1 or MSCsup2) or the aforementioned control medium diluted to ½ with a culturing medium was dispensed into each well. After 24 hours or after 48 hours, the cells were recovered, RNA was separated therefrom by a routine method, the expression levels of TGFβ and COL3A1 were checked by real-time PCR, and their expression intensities calculated on the assumption that the expression intensity obtained in using the control is 1 are shown in FIGS. 5 and 6.

The culture supernatant of the mesenchymal stem cells of the present invention acted on the human vascular endothelial cells HUVEC, and demonstrated an effect of inhibiting the expression of TGFβ and COL3A1, that is, the genes relating to fibrosis. This suggests that the culture supernatant of the mesenchymal stem cells of the present invention is effective for diseases such as arteriosclerosis in which the fibrosis of vascular endothelial cells is involved.

(Anti-Inflammatory Action and Fibrosis Inhibition Action of Culture Supernatant on Human Lung Epithelial Carcinoma Cells)

Figure 7:
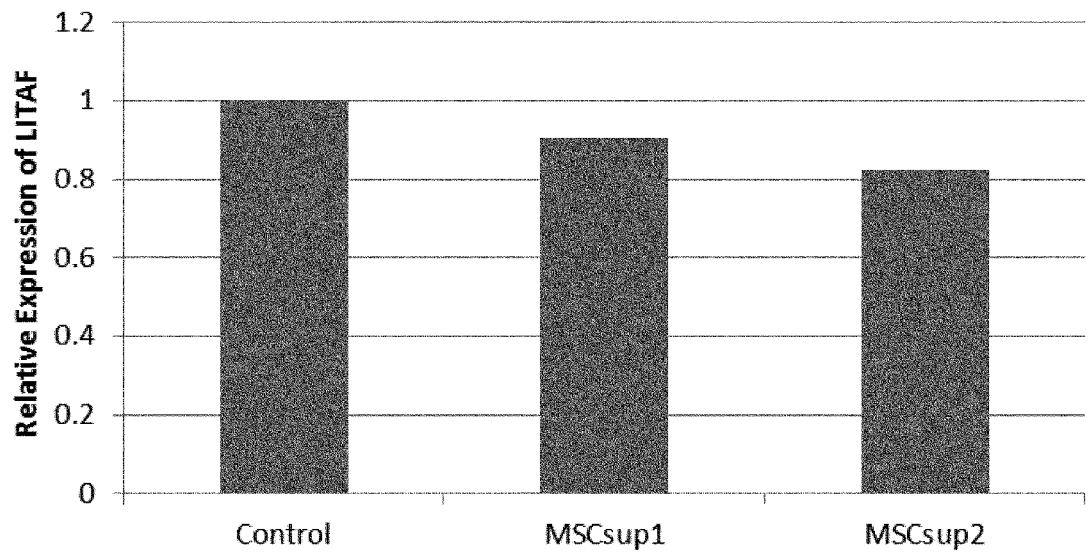
FIG. 7 is a bar graph indicating the anti-inflammatory effect on human lung epithelial carcinoma cells of culture supernatants of the mesenchymal stem cells of the present invention.
Figure 8:
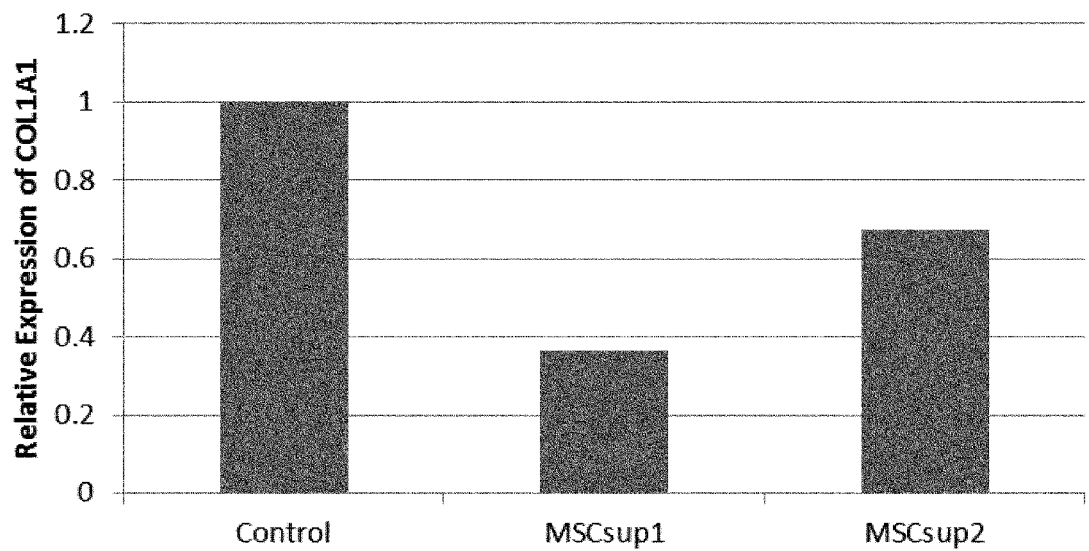
FIG. 8 is a bar graph indicating the anti-fibrotic effect on human lung epithelial carcinoma cells of culture supernatants of the mesenchymal stem cells of the present invention.
Figure 9:
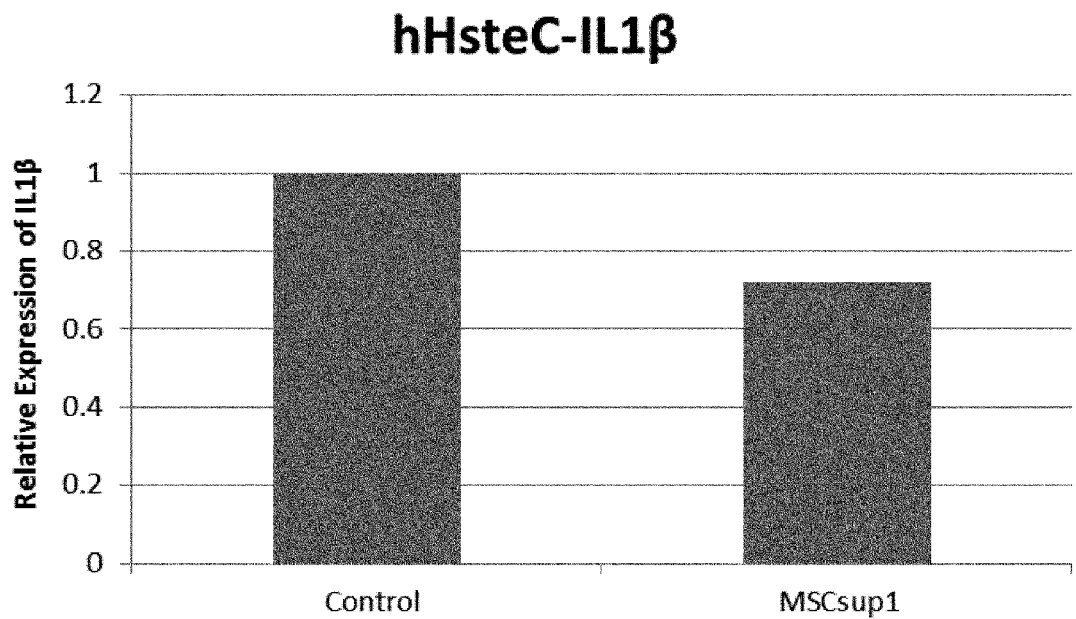
FIG. 9 is a bar graph indicating the anti-inflammatory effect on human hepatic stellate cells of culture supernatants of the mesenchymal stem cells of the present invention.
Figure 10:
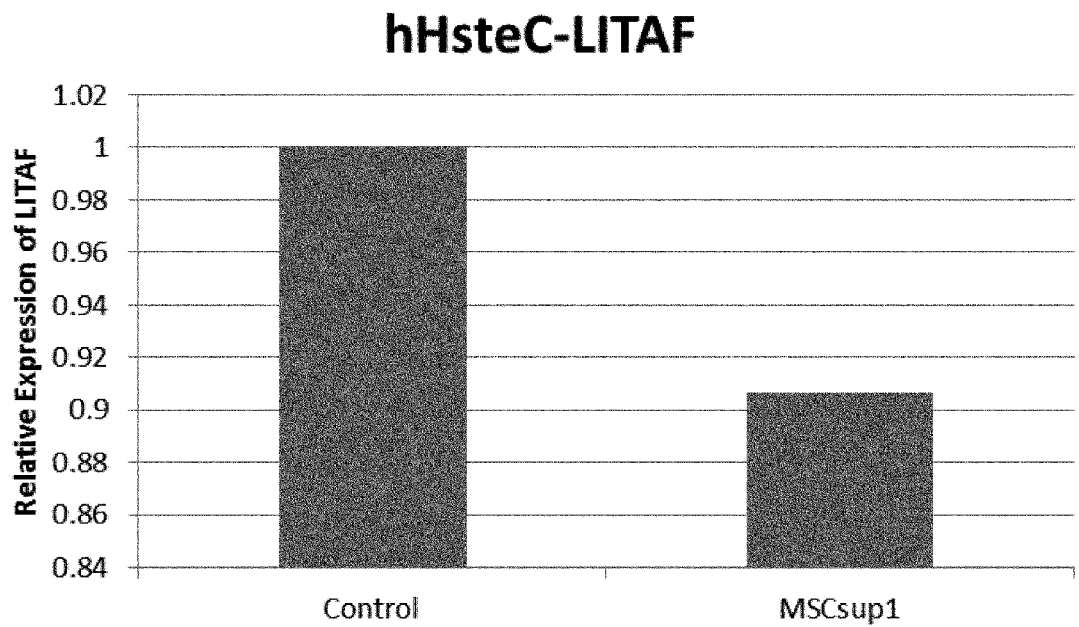
FIG. 10 is a bar graph indicating the anti-inflammatory effect on human hepatic stellate cells of culture supernatants of the mesenchymal stem cells of the present invention.
Figure 11:
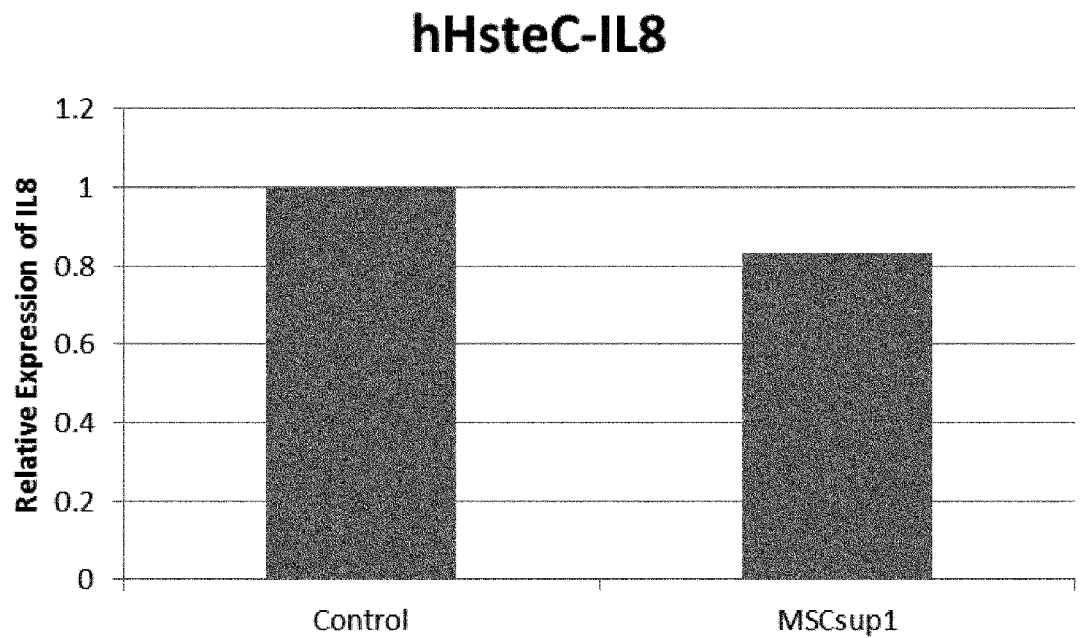
FIG. 11 is a bar graph indicating the anti-inflammatory effect on human hepatic stellate cells of culture supernatants of the mesenchymal stem cells of the present invention.
Figure 12:
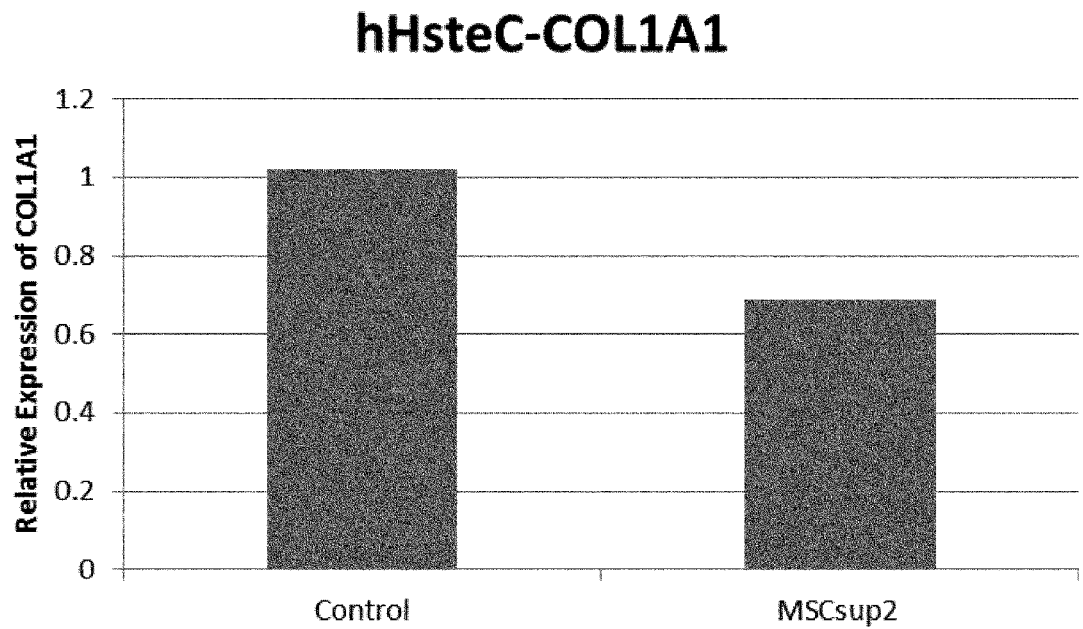
FIG. 12 is a bar graph indicating the anti-fibrotic effect on human hepatic stellate cells of culture supernatants of the mesenchymal stem cells of the present invention.

Human lung epithelial carcinoma cell line A549 was seeded into a 6-well plate at $1\times10^5$ cells/well, the medium was removed on the following day, and the aforementioned culture supernatant (MSCsup1 or MSCsup2), the aforementioned control medium, any of these media diluted to ½ with a culturing medium, the aforementioned culturing medium (MSCsup1 or MSCsup2) alone, or the aforementioned control medium alone was dispensed into each well. After 24 hours, the cells were recovered, RNA was separated therefrom by a routine method, the expression levels of LITAF and COL1A1 were checked by the real-time PCR, and their expression intensities calculated on the assumption that the expression intensity obtained in using the control is 1 are illustrated in FIGS. 7 and 8.

The culture supernatant of the mesenchymal stem cells of the present invention acted on the human lung epithelial carcinoma cell line A549, and demonstrated an effect of inhibiting the expression of LITAF, that is, the gene relating to inflammation, and COL1A1, that is, the genes relating to fibrosis. This suggests that the culture supernatant of the mesenchymal stem cells of the present invention is effective for diseases such as lung/respiratory inflammation and chronic obstructive pulmonary disease (COPD) in which inflammation and fibrosis of lung epithelial cells are involved.

(Anti-Inflammatory Action and Fibrosis Inhibition Action of Culture Supernatant on Human Hepatic Stellate Cells)

Human hepatic stellate cells (hHsteC) were seeded into a 6-well plate at $1\times10^5$ cells/well, the medium was removed on the following day, and the aforementioned culture supernatant (MSCsup1 or MSCsup2) or the aforementioned control medium was dispensed into each well. After 24 hours, LPS was added to a concentration of 100 ng/mL, the cells were recovered 24 hours after the addition, RNA was separated therefrom by a routine method, the expression levels of IL-1β, LITAF, IL-8 and COL1A1 were checked by the real-time PCR, and their expression intensities calculated on the assumption that the expression intensity obtained in using the control is 1 are illustrated in FIGS. 9 to 12.

The culture supernatant of the mesenchymal stem cells of the present invention acted on the human hepatic stellate cells hHsteC, and demonstrated an effect of inhibiting the expression of IL-1β, LITAF, IL-8, that is, the genes relating to inflammation, and COL1A1, that is, the genes relating to fibrosis. This suggests that the culture supernatant of the mesenchymal stem cells of the present invention is effective for diseases such as lung/respiratory inflammation and chronic obstructive pulmonary disease (COPD) in which inflammation and fibrosis of hepatic stellate cells are involved.

(Anti-Inflammatory Action and Fibrosis Inhibition Action of Culture Supernatant on Human Cardiac Myocytes)

Figure 13:
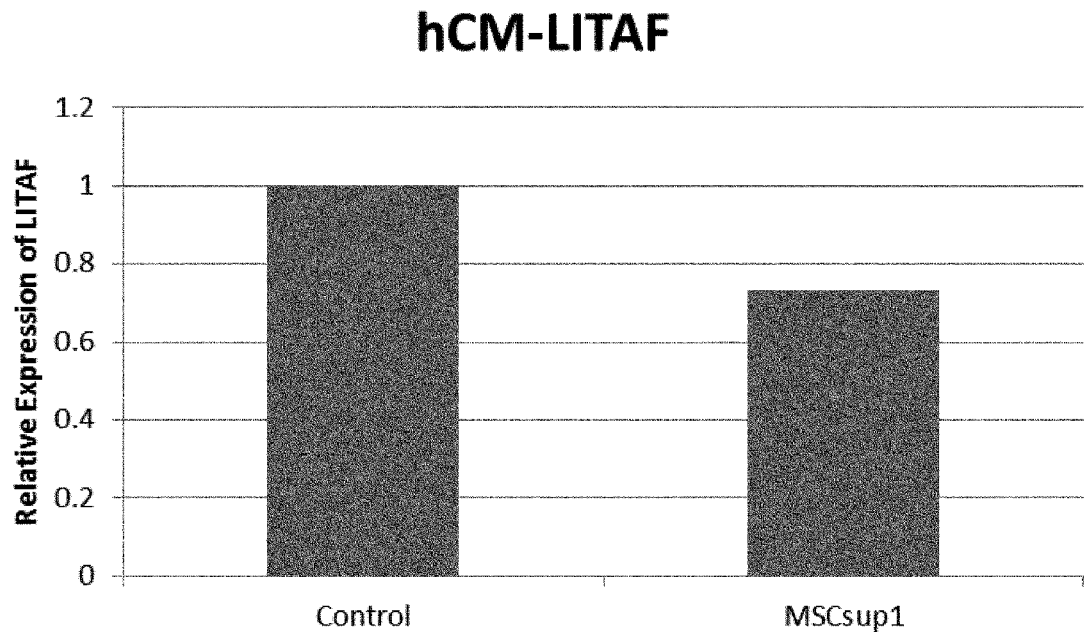
FIG. 13 is a bar graph indicating the anti-inflammatory effect on human cardiac myocytes of culture supernatants of the mesenchymal stem cells of the present invention.
Figure 14:
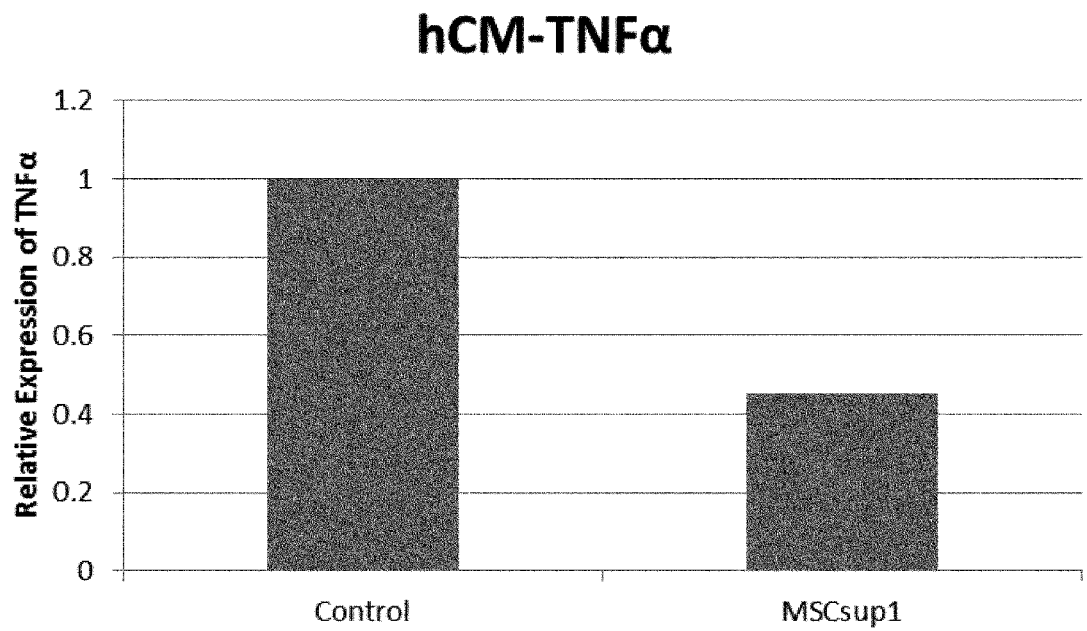
FIG. 14 is a bar graph indicating the anti-inflammatory effect on human cardiac myocytes of culture supernatants of the mesenchymal stem cells of the present invention.
Figure 15:
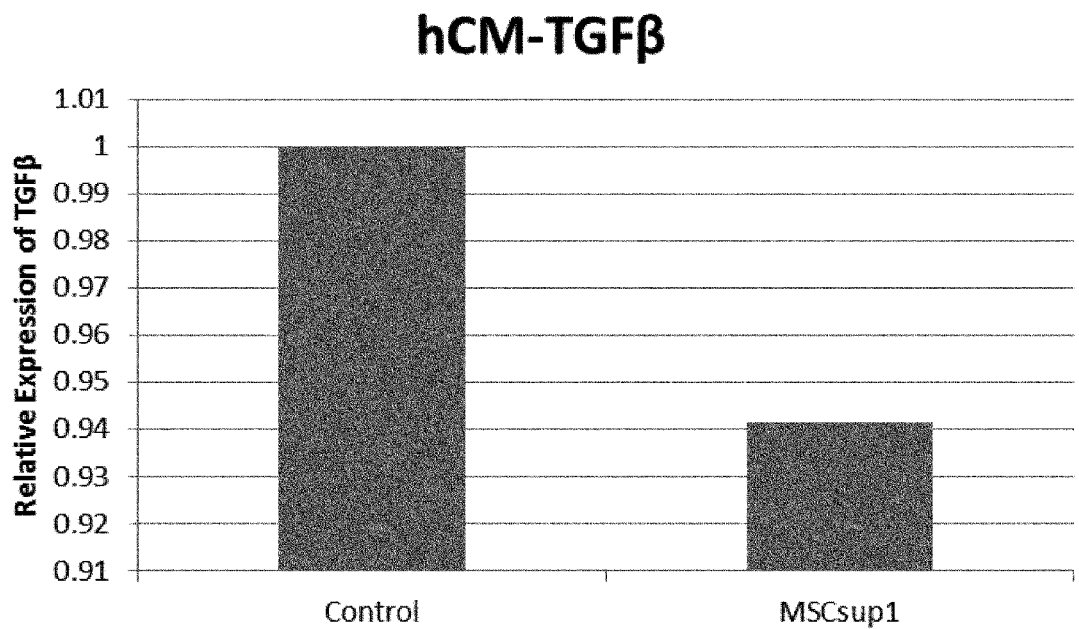
FIG. 15 is a bar graph indicating the anti-fibrotic effect on human cardiac myocytes of culture supernatants of the mesenchymal stem cells of the present invention.

Human cardiac myocytes (hCM) were seeded into a 6-well plate at $1\times10^5$ cells/well, the medium was removed on the following day, and the aforementioned culture supernatant (MSCsup1) or the aforementioned control medium was dispensed into each well. After 48 hours, the cells were recovered, RNA was separated therefrom by a routine method, the expression levels of LITAF, TNFα and TGFβ were checked by the real-time PCR, and their expression intensities calculated on the assumption that the expression intensity obtained in using the control is 1 are illustrated in FIGS. 13 to 15.

The culture supernatant of the mesenchymal stem cells of the present invention acted on the human cardiac myocytes hCM, and demonstrated an effect of inhibiting the expression of LITAF and TNFα, that is, the genes relating to inflammation, and TGFβ, that is, the gene relating to fibrosis. This suggests that the culture supernatant of the mesenchymal stem cells of the present invention is effective for diseases such as myocarditis and cardiac hypertrophy in which inflammation and fibrosis of cardiac myocytes are involved.

(Anti-Inflammatory Action and Fibrosis Promotion Action of Culture Supernatant on Human Gingival Fibroblasts)

Figure 16:
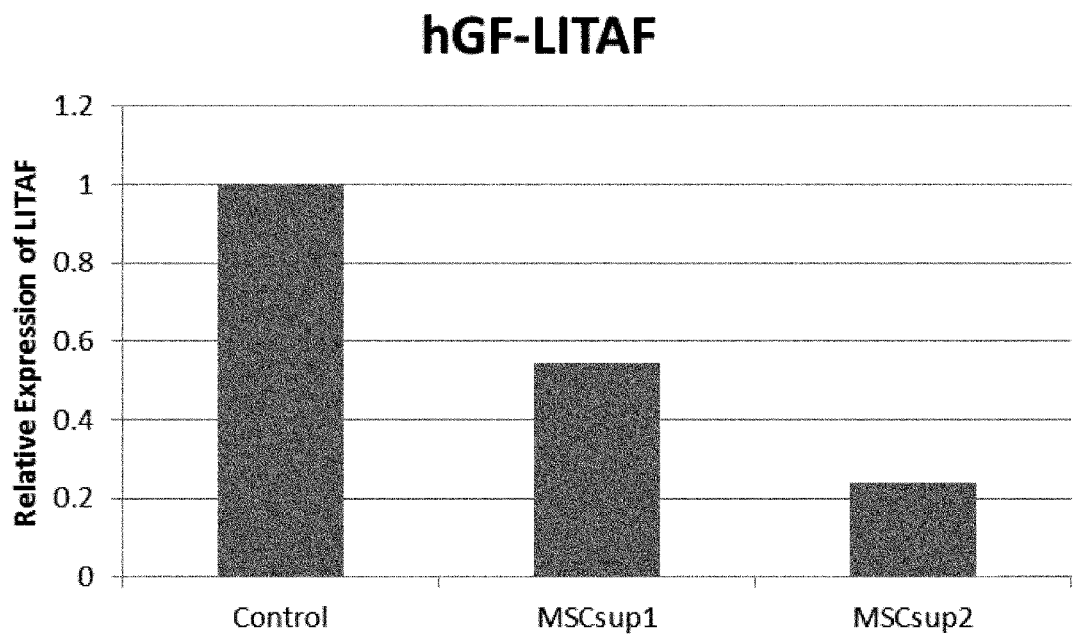
FIG. 16 is a bar graph indicating the anti-inflammatory effect on human gingival fibroblasts of culture supernatants of the mesenchymal stem cells of the present invention.
Figure 17:
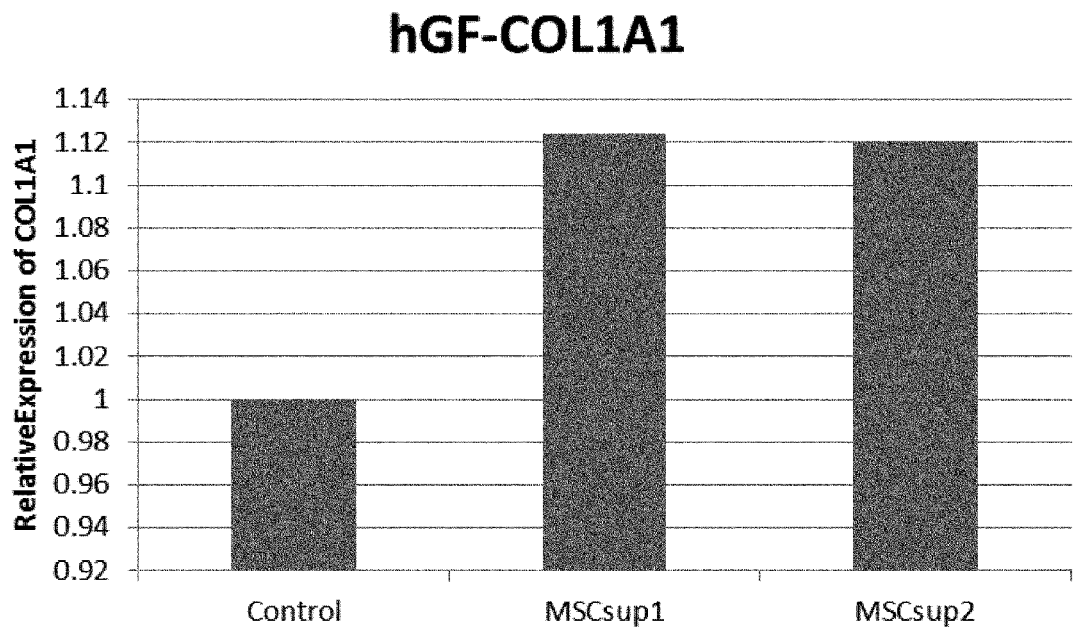
FIG. 17 is a bar graph indicating the gingival recession inhibitory effect on human gingival fibroblasts of culture supernatants of the mesenchymal stem cells of the present invention.
Figure 18:
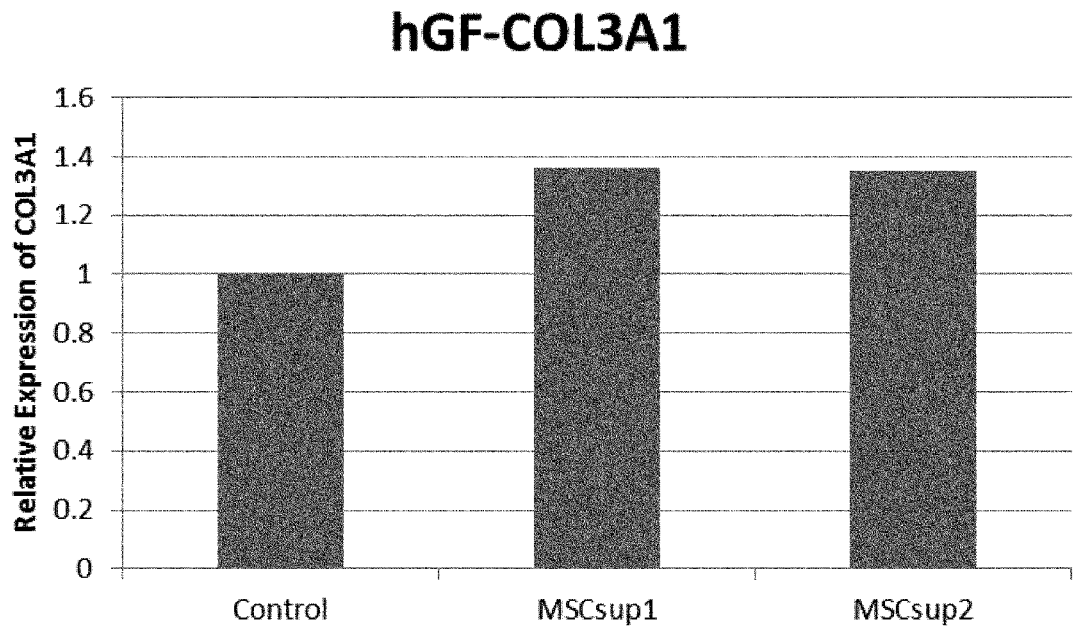
FIG. 18 is a bar graph indicating the gingival recession inhibitory effect on human gingival fibroblasts of culture supernatants of the mesenchymal stem cells of the present invention.

Human gingival fibroblasts (hGF) were seeded into a 6-well plate at $1\times10^5$ cells/well, the medium was removed on the following day, and the aforementioned culture supernatant (MSCsup1 or MSCsup2) or the aforementioned control medium was dispensed into each well. After 48 hours, the cells were recovered, RNA was separated therefrom by a routine method, the expression levels of LITAF, COL1A1 and COL3A1 were checked by the real-time PCR, and their expression intensities calculated on the assumption that the expression intensity obtained in using the control is 1 are illustrated in FIGS. 16 to 18. With respect to hGF, it is regarded that fibrosis is preferably promoted to improve periodontal disease. In other words, when the expression of COL1A1 and COL3A1 is enhanced, it can be determined that an effect of improving periodontal disease is obtained.

The culture supernatant of the mesenchymal stem cells of the present invention acted on the human gingival fibroblasts hGF, and demonstrated effects of inhibiting the expression of LITAF, that is, the gene relating to inflammation, and enhancing the expression of COL1A1 and COL3A1, that is, the genes relating to fibrosis. This suggests that the culture supernatant of the mesenchymal stem cells of the present invention is effective for prevention and/or treatment of periodontal disease.

INDUSTRIAL APPLICABILITY

Mesenchymal stem cells expressing at least one cell surface marker selected from the group consisting of CD201, CD46, CD56, CD147 and CD165 are characterized as cells which, in addition to demonstrating superior actions to inhibit the production of inflammatory cytokines from macrophages and other immune cells, and to enhance barrier function, are resistant to oxidative stress and less susceptible to damage. In addition, a culture supernatant of the mesenchymal stem cells expressing the aforementioned specific marker acts on cardiac myocytes, vascular endothelial cells, lung epithelial carcinoma cells, hepatic stellate cells, gingival fibroblasts and the like to demonstrate an effect of appropriately adjusting expression of genes relating to inflammation and fibrosis. Consequently, a pharmaceutical composition of the present invention, which contains the mesenchymal stem cells, demonstrates superior therapeutic effects against various diseases such as cancer, precancerous symptoms, inflammatory diseases, immune diseases, neurodegenerative diseases, metabolic diseases, cardiovascular diseases, heart diseases, bone diseases, gastrointestinal diseases, lung diseases, liver diseases, kidney diseases and oral diseases.

The invention claimed is:

1. A method for treating a disease or medical condition, comprising administering mesenchymal stem cells or culture supernatant thereof to a subject,
wherein the mesenchymal stem cells express at least one cell surface marker selected from the group consisting of CD201, CD46, CD56, CD147 and CD165 and are derived from umbilical cord, adipose or bone marrow, and wherein the mesenchymal stem cells are positive for CD29, CD73, CD90, CD105, and CD166.

2. The method for treating a disease according to claim 1, wherein the medical condition is selected from the group consisting of cancer, precancerous symptoms, inflammatory diseases, cardiovascular diseases, heart diseases, lung diseases, liver diseases and oral diseases.

3. The method for treating a disease according to claim 1, wherein the medical condition is selected from the group consisting of lung cancer, myocarditis, cardiac hypertrophy, arteriosclerosis, lung/respiratory inflammation, chronic obstructive pulmonary disease (COPD), hepatitis, liver cirrhosis and periodontal disease.

4. The method for treating a disease according to claim 1, wherein the mesenchymal stem cells secrete Crossveinless-2 and Ectodysplasin A2.

5. The method for treating a disease according to claim 4, wherein the mesenchymal stem cells further secrete at least one selected from the group consisting of activin A, Dkk-3, decorin, HGF, Dkk-1, progranulin, GDF-15, angiopoietin-1, CCL28 (VIC), latent TGF-β binding protein 1 (Latent TGF-beta bp1), GDF1, VEGF-C, BTC (betacellulin), Nidogen-1, GLO-1 (glyoxalase-1), sgp130 (soluble gp130), Chordin-Like 2 and EMAP-II.

6. The method for treating a disease according to claim 1, wherein the subject has a medical condition selected from the group consisting of cancer, precancerous symptoms, inflammatory diseases, immune diseases, neurodegenerative diseases, metabolic diseases, cardiovascular diseases, heart diseases, bone diseases, gastrointestinal diseases, lung diseases, liver diseases, kidney diseases, and oral diseases.

* * * * *